(12) United States Patent
Kodama

(10) Patent No.: US 12,263,497 B2
(45) Date of Patent: Apr. 1, 2025

(54) ELECTROSTATIC SPRAY DEVICE, CARTRIDGE, AND COVER

(71) Applicant: KAO CORPORATION, Tokyo (JP)

(72) Inventor: Shinji Kodama, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 602 days.

(21) Appl. No.: 17/614,696

(22) PCT Filed: May 22, 2020

(86) PCT No.: PCT/JP2020/020413
§ 371 (c)(1),
(2) Date: Nov. 29, 2021

(87) PCT Pub. No.: WO2020/241526
PCT Pub. Date: Dec. 3, 2020

(65) Prior Publication Data
US 2022/0161282 A1 May 26, 2022

(30) Foreign Application Priority Data

May 31, 2019 (JP) ................................. 2019-103334
May 22, 2020 (JP) ................................. 2020-089479

(51) Int. Cl.
*B05B 5/035* (2006.01)
*B05B 5/053* (2006.01)
(Continued)

(52) U.S. Cl.
CPC ............ *B05B 5/035* (2013.01); *B05B 5/0533* (2013.01); *B05B 5/0535* (2013.01); *B05B 5/1691* (2013.01); *A61M 35/003* (2013.01)

(58) Field of Classification Search
None
See application file for complete search history.

(56) References Cited

U.S. PATENT DOCUMENTS 3,941,312 A * 3/1976 Ohno .................... B41J 2/1606
  239/102.1
4,255,777 A * 3/1981 Kelly .................... B05B 5/0533
  361/228
(Continued)

FOREIGN PATENT DOCUMENTS

CN     104245148 A    12/2014
EP     2 974 749 B1   11/2016
(Continued)

OTHER PUBLICATIONS

Extended European Search Report issued Jun. 6, 2023, in corresponding European Patent Application No. 20815286.8, 11 pages.
(Continued)

*Primary Examiner* — Binu Thomas
(74) *Attorney, Agent, or Firm* — Oblon, McClelland, Maier & Neustadt, L.L.P.

(57) ABSTRACT

Provided is a hand-held type electrostatic spray device (1) spraying an electrically charged liquid, the electrostatic spray device (1) comprising: a voltage source; a needle-shaped electrode (53: a base electrode) for electrically charging the liquid to which a voltage is applied from the voltage source and which includes a linear tip portion; a second bottom portion (32: an additional electrode) of a second electrode member (3) to which a voltage is applied from the voltage source; and a conductor (6) which is electrically isolated from the second bottom portion (32) and the needle-shaped electrode (53) and is disposed on a spray side of the liquid from the second bottom portion (32), at least a part of the conductor (6) overlapping with the second bottom portion (32) in a direction orthogonal to a spray direction of the liquid.

17 Claims, 12 Drawing Sheets

(51) Int. Cl.
*B05B 5/16* (2006.01)
*A61M 35/00* (2006.01)

(56) References Cited

U.S. PATENT DOCUMENTS

| | | | |
|---|---|---|---|
| 5,044,564 A * | 9/1991 | Sickles | B05B 5/0533 |
| | | | 239/707 |
| 6,318,647 B1 * | 11/2001 | Gaw | B05B 5/1691 |
| | | | 239/708 |
| 2004/0021017 A1 | 2/2004 | Sumiyoshi et al. | |
| 2006/0064892 A1 | 3/2006 | Matsui et al. | |
| 2007/0114305 A1 | 5/2007 | Yamaguchi et al. | |
| 2007/0176029 A1 * | 8/2007 | Yamaguchi | B05B 5/1691 |
| | | | 239/690 |
| 2012/0175440 A1 * | 7/2012 | Uegaki | B05B 5/057 |
| | | | 239/690 |
| 2013/0092765 A1 | 4/2013 | Kelly | |
| 2014/0117123 A1 * | 5/2014 | Kelly | B05B 5/1691 |
| | | | 239/708 |
| 2016/0031708 A1 * | 2/2016 | Machi | B05B 5/0533 |
| | | | 422/186.2 |
| 2019/0153623 A1 | 5/2019 | Sugawara et al. | |

FOREIGN PATENT DOCUMENTS

| | | |
|---|---|---|
| JP | 2005-518278 A | 6/2005 |
| JP | 2005-288212 A | 10/2005 |
| JP | 2007-521941 A | 8/2007 |
| JP | 2009-39608 A | 2/2009 |
| JP | 4415014 B2 | 2/2010 |
| JP | 2013-94719 A | 5/2013 |
| JP | 2014-534900 A | 12/2014 |
| JP | 6196223 B2 | 9/2017 |
| WO | WO 91/15673 A1 | 10/1991 |

OTHER PUBLICATIONS

International Search Report issued on Jul. 28, 2020 in PCT/JP2020/020413 filed May 22, 2020, 2 pages.

* cited by examiner

ELECTROSTATIC SPRAY DEVICE, CARTRIDGE, AND COVER

CROSS-REFERENCE TO RELATED APPLICATIONS

The present application claims the benefit of priority to claims the benefit of priority to International Application No. PCT/JP2020/020413, filed May 22, 2022, which is based upon and claims the benefit of priority to Japanese Application No. JP 2020-089479, filed May 22, 2020, and Japanese Application No. JP 2019-103334, filed May 31, 2019. The entire contents of these applications are incorporated herein by reference.

FIELD OF THE INVENTION

The present invention relates to an electrostatic spray device.

BACKGROUND OF THE INVENTION

In the related art, an electrostatic spray device spraying an electrically charged liquid toward a target is known. For example, in JP 2007-521941 A, an electrostatic spray device which is made with a dimension that a user is capable of holding with a hand and imparts a liquid composition to which a high voltage is applied from an emitter electrode connected to a high-voltage generator toward the skin of the user from the nozzle is described. The emitter electrode includes a central antenna. The central antenna extends into a nozzle passage and charges the liquid composition.

SUMMARY OF THE INVENTION

The present invention relates to a hand-held type electrostatic spray device which has a shape or a size that a user is capable of retaining with a hand and sprays an electrically charged liquid, the electrostatic spray device comprising: a voltage source; a base electrode for electrically charging the liquid to which a voltage is applied from the voltage source and which includes a linear tip portion; an additional electrode to which a voltage is applied from the voltage source; and a conductor which is electrically isolated from the base electrode and the additional electrode and is disposed on a spray side of the liquid from the additional electrode, at least a part of the conductor overlapping with the additional electrode in a direction orthogonal to a spray direction of the liquid.

In addition, the present invention relates to a cartridge of a hand-held type electrostatic spray device which has a shape or a size that a user is capable of retaining with a hand and sprays an electrically charged liquid, the cartridge comprising: a base electrode for electrically charging the liquid to which a voltage is capable of being applied from a voltage source and which includes a linear tip portion; an additional electrode to which a voltage is capable of being applied from the voltage source; and a conductor which is electrically isolated from the base electrode and the additional electrode and is disposed on a spray side of the liquid from the additional electrode, at least a part of the conductor overlapping with the additional electrode in a direction orthogonal to a spray direction of the liquid.

Further, the present invention relates to a cover of a hand-held type electrostatic spray device which has a shape or a size that a user is capable of retaining with a hand and sprays an electrically charged liquid, a main body of the electrostatic spray device, including: a voltage source; a base electrode for electrically charging the liquid to which a voltage is applied from the voltage source and which includes a linear tip portion; and an additional electrode to which a voltage is applied from the voltage source, the cover being attachable and detachable with respect to the main body, the cover comprising a conductor, and the conductor being disposed on a spray side of the liquid from the additional electrode and being electrically isolated from the base electrode and the additional electrode, and at least a part of the conductor overlapping with the additional electrode in a direction orthogonal to a spray direction of the liquid, in a state in which the cover is mounted on the main body.

DETAILED DESCRIPTION OF THE INVENTION

Figure 1:
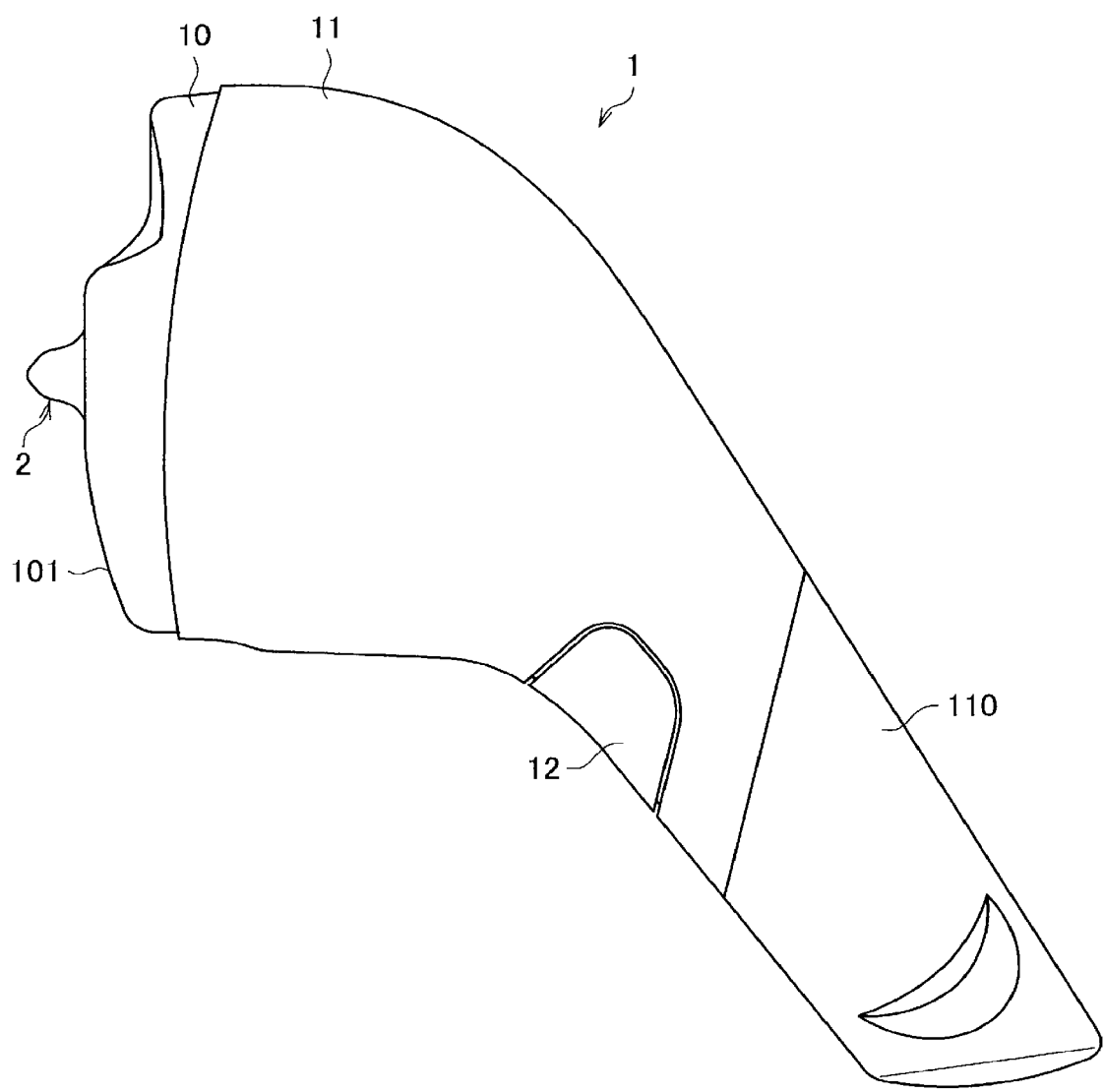
FIG. 1 is a side view of an electrostatic spray device according to a first embodiment of the present invention.

In a hand-held type electrostatic spray device having a shape or a size that a user is capable of retaining with a hand, there are various liquids to be used, various spray targets, or various environments in which the device is used, and the height of a voltage that can be used is also limited. Accordingly, it has been aspired to improve the straightness of a liquid to be sprayed or the content thereof (hereinafter, referred to as a liquid or the like). That is, an electrically charged liquid or the like is directed toward a target along a trajectory according to an electric field formed between the electrostatic spray device and the target. From the viewpoint of spraying the liquid to a desired position aimed by the user or from the viewpoint of efficiently spraying the liquid, it is preferable that the liquid or the like sprayed from the device progresses on a straight trajectory toward the target without being dispersed. However, it may be difficult for the liquid or the like sprayed from the device to progress straight, in accordance with the liquid to be used, the target, or the environment. In addition, the height of the voltage for forming the electric field is limited, and thus, the velocity of the liquid or the like directed toward the target is also limited, and therefore, it is not easy for the liquid or the like to progress straight.

In the electrostatic spray device described in JP 2007-521941 A, the emitter electrode includes a cylinder. In order to avoid corona discharge that is unnecessary for suitable electrostatic spray, the cylinder is provided coaxially with the central antenna to surround the nozzle passage. However, even in such a device, it is hard to say that the straightness of the liquid composition is sufficiently considered, and for example, it is not easy to allow the liquid composition to stably progress straight, in a high-humidity environment.

Therefore, the present invention relates to a hand-held type electrostatic spray device that is capable of improving straightness of a liquid or the like to be sprayed.

That is, the present invention relates to a hand-held type electrostatic spray device which has a shape or a size that a user is capable of retaining with a hand and sprays an electrically charged liquid, the device including: a voltage source; a base electrode for electrically charging the liquid to which a voltage is applied from the voltage source and includes a linear tip portion; an additional electrode to which a voltage is applied from the voltage source; and a conductor which is electrically isolated from the base electrode and the additional electrode and is disposed on a spray side of the liquid from the additional electrode, at least a part of the conductor overlapping with the additional electrode in a direction orthogonal to a spray direction of the liquid.

In addition, the present invention relates to a cartridge of a hand-held type electrostatic spray device which has a shape or a size that a user is capable of retaining with a hand and sprays an electrically charged liquid, the cartridge including: a base electrode for electrically charging the liquid to which a voltage is capable of being applied from a voltage source and which includes a linear tip portion; an additional electrode to which a voltage is capable of being applied from the voltage source; and a conductor which is electrically isolated from the base electrode and the additional electrode and is disposed on a spray side of the liquid from the additional electrode, at least a part of the conductor overlapping with the additional electrode in a direction orthogonal to a spray direction of the liquid.

Further, the present invention relates to a cover of a hand-held type electrostatic spray device which has a shape or a size that a user is capable of retaining with a hand and sprays an electrically charged liquid, a main body of the electrostatic spray device, including: a voltage source; a base electrode for electrically charging the liquid to which a voltage is applied from the voltage source and which includes a linear tip portion; and an additional electrode to which a voltage is applied from the voltage source, the cover being attachable and detachable with respect to the main body, the cover including a conductor, and the conductor being disposed on a spray side of the liquid from the additional electrode and being electrically isolated from the base electrode and the additional electrode, and at least a part of the conductor overlapping with the additional electrode in a direction orthogonal to a spray direction of the liquid, in a state in which the cover is mounted on the main body.

According to an electrostatic spray device, a cartridge, and a cover of the present invention, straightness of a liquid or the like to be sprayed can be improved.

Hereinafter, preferred embodiments of the present invention will be described in detail, with reference to the accompanying drawings. Note that, in the specification and the drawings, the same reference numerals will be applied to elements having substantially the same function and configuration, and the repeated description thereof will be omitted.

First Embodiment

An electrostatic spray device 1 according to a first embodiment illustrated in FIG. 1 is a hand-held type device, and for example, has a shape, a size, and a weight that a user is capable of holding and using with one hand. An electrostatic spray method is adopted in the electrostatic spray device 1. The electrostatic spray method is a method in which a positive or negative high voltage is applied to a liquid, and thus, the liquid is electrically charged, and the electrically charged liquid is sprayed toward a target. The liquid may be a composition containing a plurality of components. The sprayed liquid spreads in a space while being repeatedly refined by a Coulomb repulsive force, and thus, is capable of forming a thin film on the surface of the target. In a case where a volatile substance is contained as a solvent of the liquid to be electrostatically sprayed, the solvent that is a volatile substance is dried while the liquid is electrostatically sprayed and ejected or after the liquid is attached to the target, and thus, a film can be formed on the surface of the target. The electrostatic spray device 1, for example, can be used in an application in which a person performs a treatment with hands, an individual application of the user, and the like, and is capable of spraying the electrically charged liquid to the target, for example, the skin or the nail of the user own or the other person. The liquid may be a liquid containing a raw material for electrostatic spinning to which a high voltage is applied, that is, a spinning liquid (a liquid composition). That is, the electrostatic spray device 1 may be an electrostatic spinning device forming a deposited material of a fiber on the surface of the target by the electrostatic spray method. It is preferable that the deposited material formed on the surface of the target is a fibrous film.

Hereinafter, the liquid (the liquid composition) used in the electrostatic spray device 1 will be described in detail. For example, a solution in which a high-molecular compound that is capable of forming a fiber, in particular, a high-molecular compound having film forming ability is dissolved in a solvent can be used as the liquid composition. Either a water-soluble high-molecular compound or a water-insoluble high-molecular compound can be used as the high-molecular compound. Water, alcohol, and ketone can be used as the solvent.

The liquid composition used in the present invention contains the following components (a), (b), and (c), and it is preferable that a mass ratio (b/c) of the component (b) to the component (c) is greater than or equal to 0.4 and less than or equal to 50.

(a) One type or two or more types of volatile substances selected from alcohol and ketone (b) High-molecular compound having film forming ability (c) Water Herein, the component (b) is a high-molecular compound selected from a water-soluble macromolecule and a water-insoluble macromolecule, and it is preferable that the component (b) is a high-molecular compound containing a water-insoluble macromolecule. Here, the "water-soluble high-molecular compound" indicates a high-molecular compound having properties in which the high-molecular compound is dipped in water having a mass of greater than or equal to 10 times that of the high-molecular compound, and the high-molecular compound is soluble in water to the extent that greater than or equal to 50 mass % of the dipped high-molecular compound is dissolved when a sufficient time (for example, longer than or equal to 24 hours) elapses, in an environment of one atmosphere and a normal temperature (20° C.±15° C.). On the other hand, the "water-insoluble high-molecular compound" indicates a high-molecular compound having properties in which the high-molecular compound is dipped in water having a mass of greater than or equal to 10 times that of the high-molecular compound, and the high-molecular compound is hardly dissolved in water to the extent that greater than or equal to 80 mass % of the dipped high-molecular compound is not dissolved when a sufficient time (for example, longer than or equal to 24 hours) elapses, in an environment of one atmosphere and a normal temperature (20° C.±15° C.).

Examples of the water-soluble high-molecular compound include mucopolysaccharide such as pullulan, a hyaluronic acid, a chondroitin sulfuric acid, a poly-γ-glutamic acid, modified cornstarch, β-glucan, glucooligosaccharide, heparin, and keratosulfate, a natural macromolecule such as cellulose, pectin, xylan, lignin, glucomannan, galacturon, psyllium seed gum, tamarind seed gum, gum arabic, tragacanth gum, modified cornstarch, soybean water-soluble polysaccharide, alginic acid, carrageenan, laminaran, agar (agarose), fucoidan, methyl cellulose, hydroxypropyl cellulose, and hydroxypropyl methyl cellulose, and a synthetic macromolecule such as partially saponified polyvinyl alcohol (in the case of not being used together with a cross-linking agent), low-saponified polyvinyl alcohol, polyvinyl pyrrolidone (PVP), polyethylene oxide, and sodium polyacrylate. Only one type of such water-soluble high-molecular compounds can be used or two or more types thereof can be used by being combined. Among such water-soluble high-molecular compounds, it is preferable to use the pullulan and the synthetic macromolecule such as the partially saponified polyvinyl alcohol, the low-saponified polyvinyl alcohol, the polyvinyl pyrrolidone, and the polyethylene oxide, from the viewpoint of easily forming a film.

On the other hand, examples of the water-insoluble high-molecular compound include completely saponified polyvinyl alcohol that can be subjected to an insoluble treatment after forming a film or a fiber, partially saponified polyvinyl alcohol that can be subjected to a cross-linking treatment after forming a fiber by being used together with a cross-linking agent, oxazoline modified silicone such as a poly(N-propanoyl ethylene imine) graft-dimethyl siloxane/γ-aminopropyl methyl siloxane copolymer, zein (a main component of corn protein), polyester, a polylactic acid (PLA), an acrylic resin such as a polyacrylonitrile resin and a polymethacrylate resin, a polystyrene resin, a polyvinyl butyral resin, a polyethylene terephthalate resin, a polybutylene terephthalate resin, a polyurethane resin, a polyamide resin, a polyimide resin, and a polyamide imide resin. Only one type of such water-insoluble high-molecular compounds can be used or two or more types thereof can be used by being combined. Preferably, among such water-insoluble macromolecules, it is preferable to use one type or two or more types selected from the completely saponified polyvinyl alcohol that can be subjected to the insoluble treatment after forming the film, the partially saponified polyvinyl alcohol that can be subjected to the cross-linking treatment after forming the film by being used together with the cross-linking agent, the polyvinyl butyral resin, the acrylic resin such as the polymethacrylate resin, polyvinyl acetal diethyl aminoacetate, the oxazoline modified silicone such as the poly(N-propanoyl ethylene imine) graft-dimethyl siloxane/γ-aminopropyl methyl siloxane copolymer, the polylactic acid (PLA), the zein, and the polyurethane.

It is preferable that the component (b) is the water-insoluble high-molecular compound from the viewpoint of being dissolved or dispersed in the component (a) and of forming a fiber on the skin, the nail, or the like, and the liquid composition functions as the spinning liquid. The component (b) being dissolved or dispersed indicates that a dispersed state thereof is a visually homogeneous state, preferably, a visually transparent or semi-transparent state.

The volatile substance of the component (a) is a substance having volatility in a liquid state. In a case where the liquid composition placed in an electric field is sufficiently electrically charged, and then, is ejected toward the skin from a nozzle tip, and the component (a) is evaporated, a charge density of the liquid composition becomes excessive, the component (a) is further evaporated while being further refined by Coulomb repulsion, and finally a film containing a dried fiber is formed, and thus, the component (a) is blended in the liquid composition. For this reason, a vapor pressure of the volatile substance at 20° C. is preferably greater than or equal to 0.01 kPa and less than or equal to 106.66 kPa, is more preferably greater than or equal to 0.13 kPa and less than or equal to 66.66 kPa, is even more preferably greater than or equal to 0.67 kPa and less than or equal to 40.00 kPa, and is still even more preferably greater than or equal to 1.33 kPa and less than or equal to 40.00 kPa.

Among the volatile substances of the component (a), for example, monovalent chain aliphatic alcohol, monovalent cyclic aliphatic alcohol, and monovalent aromatic alcohol are preferably used as the alcohol. Examples of the monovalent chain aliphatic alcohol include C1-C6 alcohol, examples of the monovalent cyclic alcohol include C4-C6 cyclic alcohol, and examples of the monovalent aromatic alcohol include benzyl alcohol and phenyl ethyl alcohol. Specific examples thereof include ethanol, isopropyl alcohol, butyl alcohol, phenyl ethyl alcohol, n-propanol, and n-pentanol. One type or two or more types selected from such alcohols can be used.

Among the volatile substances of the component (a), examples of the ketone include di C1-C4 alkyl ketone such as acetone, methyl ethyl ketone, and methyl isobutyl ketone. Only one type of such ketones can be used or two or more types thereof can be used by being combined.

The volatile substance of the component (a) is preferably one type or two or more types selected from ethanol, isopropyl alcohol, and butyl alcohol, is more preferably one type or two types selected from ethanol and butyl alcohol, and is even more preferably ethanol.

The content of the component (a) in the liquid composition is preferably greater than or equal to 50 mass %, is more preferably greater than or equal to 55 mass %, is even more preferably greater than or equal to 60 mass %, and is still even more preferably greater than or equal to 65 mass %. In addition, the content of the component (a) in the liquid composition is preferably less than or equal to 95 mass %, is more preferably less than or equal to 94 mass %, is even more preferably less than or equal to 93 mass %, and is still even more preferably less than or equal to 92 mass %. The content of the component (a) in the liquid composition is preferably greater than or equal to 50 mass % and less than or equal to 95 mass %, is more preferably greater than or equal to 55 mass % and less than or equal to 94 mass %, is even more preferably greater than or equal to 60 mass % and less than or equal to 93 mass %, and is still even more preferably greater than or equal to 65 mass % and less than or equal to 92 mass %. By containing the component (a) in the liquid composition at such a ratio, the component (a) in the liquid composition can be sufficiently volatilized at the time of performing the electrostatic spray method, and a film containing a fiber in which the component (b) is a main component can be formed on the surface of the skin or the nail.

It is preferable that the high-molecular compound of the component (b) is the water-insoluble polymer from the viewpoint of fiber forming properties, and the high-molecular compound is a substance that can be dissolved in the volatile substance of the component (a). Here, being dissolved indicates that the high-molecular compound is in a dispersed state at 20° C. and the dispersed state is a visually homogeneous state, preferably, a visually transparent or semi-transparent state.

As the water-insoluble polymer for forming a fiber, a suitable water-insoluble polymer is used in accordance with the properties of the volatile substance of the component (a). Specifically, the water-insoluble polymer is a polymer that is soluble in the component (a), preferably, insoluble in water. Herein, a "water-soluble polymer" indicates a water-soluble polymer having properties in which 1 g of the polymer is weighed, and then, is dipped in 10 g of ion exchange water, and greater than or equal to 0.5 g of the dipped polymer is dissolved in water after 24 hours elapse, in an environment of one atmosphere and 23° C. On the other hand, herein, the "water-insoluble polymer" indicates a water-insoluble polymer having properties in which 1 g of the polymer is weighed, and then, is dipped in 10 g of ion exchange water, and greater than or equal to 0.5 g of the dipped polymer is not dissolved after 24 hours elapse, in other words, a dissolution amount is less than 0.5 g, in an environment of one atmosphere and 23° C.

The content of the component (b) in the liquid composition is preferably greater than or equal to 4 mass %, is more preferably greater than or equal to 6 mass %, and is even more preferably greater than or equal to 8 mass %, from the viewpoint of film forming properties. In addition, the content of the component (b) is preferably less than or equal to 40 mass %, is more preferably less than or equal to 35 mass %, and is even more preferably less than or equal to 30 mass %, from the viewpoint of electrostatic spray properties. The content of the component (b) in the liquid composition is preferably greater than or equal to 4 mass % and less than or equal to 35 mass %, is more preferably greater than or equal to 6 mass % and less than or equal to 30 mass %, and is even more preferably greater than or equal to 8 mass % and less than or equal to 25 mass %. In the case of forming a film that is a deposited material of a fiber, it is possible to stably efficiently form the film that is the deposited material of the fiber by containing the component (b) in the liquid composition at such a ratio.

The water in the component (c) is ionized and charged compared to a solvent such as ethanol that is not ionized, and thus, is capable of imparting conductivity to the liquid composition. For this reason, a fibrous film is stably formed on the surface of the skin or the nail by electrostatic spray.

In addition, the water contributes to the improvement of the adhesiveness of a film to be formed by the electrostatic spray with respect to the skin or the nail and the improvement of durability. From the viewpoint of obtaining such function effects, the content of the component (c) in the liquid composition is greater than or equal to 0.2 mass % and less than or equal to 25 mass %. The content of the component (c) in the liquid composition is preferably greater than or equal to 0.3 mass %, is more preferably greater than or equal to 0.35 mass %, and is even more preferably greater than or equal to 0.4 mass %. In addition, the content of the component (c) in the liquid composition is preferably less than or equal to 20 mass %, is more preferably less than or equal to 19 mass %, and is even more preferably less than or equal to 18 mass %. The content of the component (c) in the liquid composition is greater than or equal to 0.2 mass % and less than or equal to 25 mass %, is preferably greater than or equal to 0.3 mass % and less than or equal to 20 mass %, is more preferably greater than or equal to 0.35 mass % and less than or equal to 19 mass %, and is even more preferably greater than or equal to 0.4 mass % and less than or equal to 18 mass %.

In addition, the mass ratio (b/c) of the component (b) to the component (c) is greater than or equal to 0.4 and less than or equal to 50, from the viewpoint of the film forming properties with respect to the surface of the target such as the skin, from the viewpoint of the forming properties of the fibrous film in the case of forming the fiber, from the viewpoint of improving the adhesiveness of the film with respect to the target, and from the viewpoint of improving the durability of the film. The mass ratio (b/c) is preferably greater than or equal to 0.5, and is more preferably greater than or equal to 0.6. In addition, the mass ratio (b/c) is preferably less than or equal to 45, and is more preferably less than or equal to 40. The range of the mass ratio (b/c) is greater than or equal to 0.4 and less than or equal to 50, is preferably greater than or equal to 0.5 and less than or equal to 45, is more preferably greater than or equal to 0.55 and less than or equal to 40, and is even more preferably greater than or equal to 0.6 and less than or equal to 40.

In addition, it is preferable that a mass ratio (a/c) of the component (a) to the component (c) is greater than or equal to 3 and less than or equal to 300, from the viewpoint of the film forming properties with respect to the surface of the target such as the skin, from the viewpoint of stably obtaining the fibrous film by directly electrostatically spraying the liquid composition to the target, from the viewpoint of improving the adhesiveness of the film to be obtained, from the viewpoint of improving the durability of the film, and the like. The mass ratio (a/c) is more preferably greater than or equal to 3.5, is even more preferably greater than or equal to 4. The mass ratio (a/c) is more preferably less than or equal to 250, and is even more preferably less than or equal to 210. The range of the mass ratio (a/c) is more preferably greater than or equal to 3.5 and less than or equal to 250, and is even more preferably greater than or equal to 4 and less than or equal to 210.

A mass ratio (b/a) of the component (b) to the component (a) is preferably greater than or equal to 0.01, is more preferably greater than or equal to 0.02, is even more preferably greater than or equal to 0.04, and is still even more preferably greater than or equal to 0.07, from the viewpoint of the dispersibility of the component (b) in the liquid composition and from the viewpoint of the forming properties of the film and the durability of the film. The mass ratio (b/a) is preferably less than or equal to 0.55, is more preferably less than or equal to 0.50, is even more preferably less than or equal to 0.30, and is still even more preferably less than or equal to 0.25.

In the liquid composition, only the components (a) to (c) described above may be contained, or other components may be contained in addition to the components (a) to (c). Examples of the other components include polyol, liquid oil, a plasticizer of the polymer of the component (b), an electroconductivity control agent in the liquid composition, a water-soluble polymer other than the component (b), a powder such as a coloring pigment and an extender pigment, a colorant, a perfume material, a repellent, an oxidant inhibitor, a stabilizer, an antiseptic agent, and various vitamins. In a case where the other components are contained in the liquid composition, a content ratio of the other components is preferably greater than or equal to 0.1 mass % and less than or equal to 30 mass %, and is more preferably greater than or equal to 0.5 mass % and less than or equal to 20 mass %.

In the liquid composition, the powder such as the coloring pigment and the extender pigment may be contained, and the content of the powder having a particle diameter of greater than or equal to 0.1 μm at 20° C. is preferably less than or equal to 1 mass %, is more preferably less than or equal to 0.1 mass %, and is even more preferably less than or equal to 0.01 mass %, from the viewpoint of the forming properties of a homogeneous film, and the durability and the adhesiveness of the film, but it is preferable that the powder is not contained in the liquid composition except for a case where the powder is inevitably mixed.

It is preferable that the viscosity of the liquid composition at 25° C. is 2 to 3000 mPa·s, from the viewpoint of the ease of the electrostatic spray and of stably forming the fibrous film, from the viewpoint of spinning properties at the time of performing the electrostatic spray, from the viewpoint of improving the durability of the film, and from the viewpoint of improving the touch of the film. The viscosity is preferably greater than or equal to 10 mPa·s, is more preferably greater than or equal to 20 mPa·s, and is even more preferably greater than or equal to 30 mPa·s. In addition, the viscosity is preferably less than or equal to 1500 mPa·s, is more preferably less than or equal to 1000 mPa·s, and is even more preferably less than or equal to 800 mPa·s. The range of the viscosity is preferably greater than or equal to 2 mPa·s and less than or equal to 3000 mPa·s, is more preferably greater than or equal to 20 mPa·s and less than or equal to 1500 mPa·s, is even more preferably greater than or equal to 30 mPa·s and less than or equal to 1000 mPa·s, and is still even more preferably greater than or equal to 30 mPa·s and less than or equal to 800 mPa·s. The viscosity of the liquid composition is measured at 25° C. by using an E-type viscosimeter. For example, an E-type viscosimeter (VISCONIC EMD) manufactured by TOKYO KEIKI INC. can be used as the E-type viscosimeter. As a measurement condition of such a case, 25° C. is set, a cone-plate rotor NO. 43 is used, and a suitable number of rotations according to the viscosity is selected as the number of rotations, and the number of rotations is 5 rpm in a case where the viscosity is greater than or equal to 1300 mPa·S, is 10 rpm in a case where the viscosity is greater than or equal to 250 mPa·S and less than 1300 mPa·S, is 50 rpm in a case where the viscosity is greater than or equal to 25 mPa·S and less than 250 mPa·S, and is 100 rpm in a case where the viscosity is less than 25 mPa·S.

Next, the outline of the configuration of the electrostatic spray device 1 according to this embodiment will be described with reference to FIGS. 1 to 5. As illustrated in FIG. 1, the electrostatic spray device 1 (hereinafter, simply referred to as a device 1) includes a main body side housing 11, a cover 10, and a cartridge 2. The main body side housing 11 is formed of an insulating material, and contains a battery, a motor, a high-voltage generator, a control device, and an operation switch 12. Herein, the insulating material indicates a non-conductive substance of which volume specific resistivity, for example, is greater than or equal to $10^{14}$ [Ω·cm], and is preferably greater than or equal to $10^{16}$ [Ω·cm]. An organic material such as a synthetic resin or an inorganic material such as glass or ceramic can be used as the insulating material. The main body side housing 11 includes a gripper 110. The gripper 110 is a cylindrical portion to be gripped by the user. The operation switch 12 is disposed on the gripper 110. Specifically, when the user grips the gripper 110 in order to use the device 1, the operation switch 12 is disposed in a position with which the finger of the user is in contact. It is more preferable that the operation switch 12 described below with which the finger of the user is in contact at the time of using the device 1 is formed of a conductive material. Examples of the conductive material include a metal and a mixed material of a metal and a resin.

Figure 2:
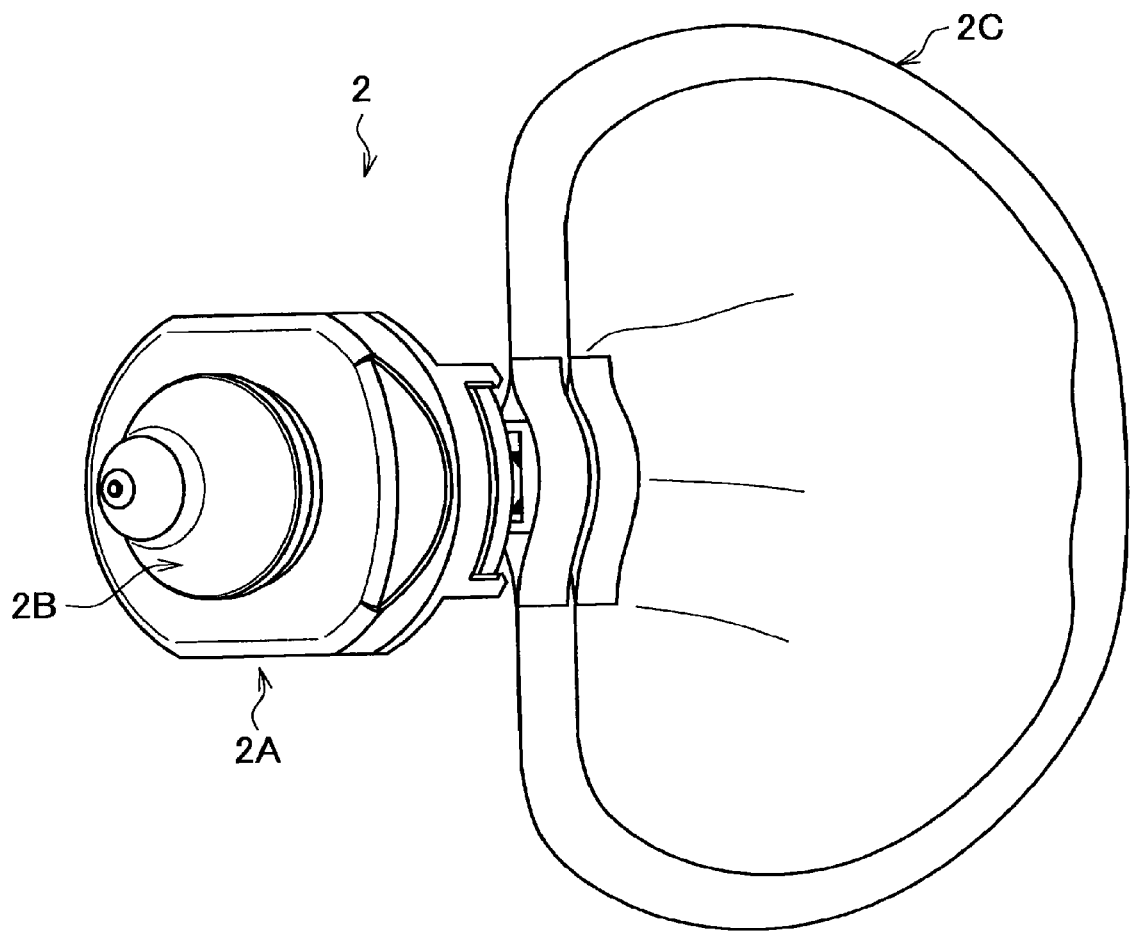
FIG. 2 is a perspective view of a cartridge of the electrostatic spray device according to the same embodiment.
Figure 3:
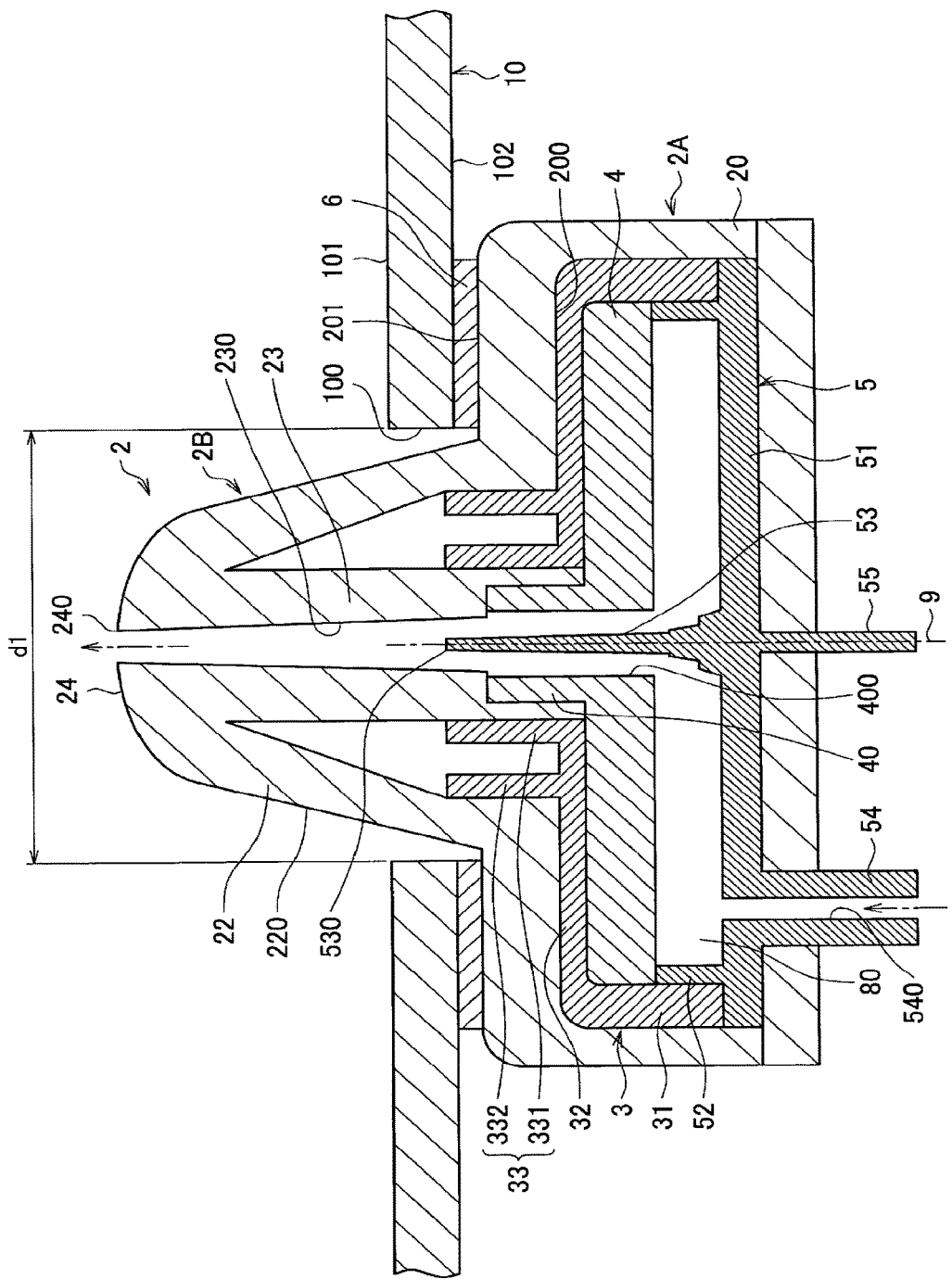
FIG. 3 is a sectional view of a part of a cover and a cartridge of an electrostatic spray device according to the first embodiment or a third embodiment of the present invention.

The cartridge 2 is detachably mounted on the main body side housing 11. As illustrated in FIGS. 2 to 6, the cartridge 2 includes a mounting portion 2A, a nozzle 2B, a container 2C, and a first conductor 6. The mounting portion 2A is a portion for mounting the cartridge 2 on the main body side housing 11, and configures the container 2C containing a liquid as the cartridge 2. Note that, in FIG. 2, the first conductor 6 is not illustrated. The cross-section of the cartridge 2 in FIG. 3 illustrates a schematic cross-section approximately corresponding to a cross-section of in FIG. 4. As illustrated in FIG. 2, the container 2C is mounted on the mounting portion 2A. The container 2C is in the shape of a flat pouch including a sheet such as a thin layered film that is formed of an insulating material, contains the liquid, and is deformable. The mounting portion 2A is detachably mounted on a mounted portion of the main body side housing 11. In a state where the mounting portion 2A is mounted on the mounted portion of the main body side housing 11, the container 2C is contained inside the main body side housing 11. The mounting portion 2A includes a cartridge side housing 20. The cartridge side housing 20 is formed of an insulating material, and a containing recess 200 is formed inside the cartridge side housing 20. In the containing recess 200, a first electrode member 5, a second electrode member 3, a pump cover 4, and a pump 8 are contained. Note that, in FIG. 3, the pump 8 is not illustrated.

The nozzle 2B of the cartridge 2 protrudes from the outer surface of the main body side housing 11. The nozzle 2B is integrally formed with the cartridge side housing 20 by the same material as that of the cartridge side housing 20. A spray port 240 is opened in a tip portion 24 of the nozzle 2B. The pump 8, for example, is a gear pump, and sucks the liquid from the container 2C and ejects the liquid toward the nozzle 2B. The first electrode member 5 is a conductor provided in a passage from the container 2C to the nozzle 2B, imparts an electric charge to the liquid flowing through the passage to be electrically charged.

The cover 10 is formed of an insulating material, and is provided on the main body side housing 11 to cover the cartridge 2 mounted on the device 1. The mounting portion 2A is retained between the cover 10 and the main body side housing 11. The cover 10 includes a hole 100 through which the nozzle 2B of the cartridge 2 mounted on the device 1 passes, and thus, in a state where the cartridge 2 is mounted on the device 1, the nozzle 2B protrudes through the hole 100 provided in the cover 10. The cover 10 covers the circumference of the nozzle 2B on the outer surface of the cartridge side housing 20. The mounting portion 2A of the cartridge 2 can be pressed against the main body side housing 11 by a circumference portion of the hole 100 on an inner surface 102 of the cover 10. The inner surface 102 of the cover 10 is a surface that is directed toward the cartridge side housing 20 side.

The battery functions as a power source that is capable of supplying power to the motor and the high-voltage generator. The motor is an electric motor for driving the pump 8. An output shaft of the motor is connected to a driving shaft of the pump 8 through a joint. The high-voltage generator, for example, includes a transformer. An output terminal of the high-voltage generator is separably connected to a terminal 55 of the first electrode member 5 of the cartridge 2. The high-voltage generator generates a direct-current high voltage by receiving the supply of a direct-current voltage from the battery and functions as a voltage source that is capable of applying the high voltage to the first electrode member 5 through the output terminal and the terminal 55. The voltage applied from the high-voltage generator may be a positive voltage, or may be a negative voltage. An earth electrode may be provided in the gripper 110 and may be exposed to be in contact with the hand of the user. The control device controls an operation state of the motor and the high-voltage generator.

The operation switch 12 is provided to be capable of switching electric connection and disconnection between the battery, and the high-voltage generator and the motor, in accordance with the manipulation of the user. That is, the operation switch 12 functions as a switch for operating the device 1. For example, in a case where the operation switch 12 is pressed, power is supplied to the motor, the high-voltage generator, and the control device from the battery. Accordingly, as illustrated by an arrow of a dashed-dotted line in FIG. 3, the liquid is sucked from the container 2C and is supplied to the nozzle 2B, and a high voltage is applied to the liquid through the first electrode member 5. The electrically charged liquid is sprayed toward the target from the spray port 240 of the nozzle 2B by a potential difference between the first electrode member 5 and the target. It is preferable to include one operation switch 12 from the viewpoint of manipulation properties of a spray operation.

In a case where the deposited material of the fiber is formed by the electrostatic spray method, the voltage to be applied to the electrode of the electrostatic spray device 1 (a spinning voltage: corresponding to the potential difference between the electrode and the target) is preferably greater than or equal to 2 kV, is more preferably greater than or equal to 5 kV, is even more preferably greater than or equal to 8 kV, and is still even more preferably greater than or equal to 10 kV, from the viewpoint of sufficiently electrically charging the liquid composition. In addition, the spinning voltage is preferably less than or equal to 30 kV, is more preferably less than or equal to 25 kV, and is even more preferably less than or equal to 20 kV, from the viewpoint of preventing discharge between the electrode and the target, and the like. From the above viewpoint, the spinning voltage is preferably greater than or equal to 5 kV and less than or equal to 30 kV, and is more preferably greater than or equal to 10 kV and is less than or equal to 25 kV.

In a case where the deposited material of the fiber is formed by the electrostatic spray method, the cross-sectional shape of the fiber is preferably a circular shape or an elliptical shape. The thickness of the fiber may be a diameter in a case where the cross-sectional shape of the fiber is the circular shape, and may be the length of a long diameter in a case where the cross-sectional shape of the fiber is the elliptical shape. The thickness of the fiber is preferably greater than or equal to 10 nm, and is more preferably greater than or equal to 50 nm, in terms of an equivalent circle diameter. In addition, the thickness of the fiber is preferably less than or equal to 3000 nm, and is more preferably less than or equal to 1000 nm. The thickness of the fiber, for example, can be measured by the following method. That is, fibers are observed at a magnification of 10000 by a scanning electron microscope (SEM), and defects (a cluster of the fibers, an intersection portion of the fibers, and a liquid droplet) are removed from two-dimensional images thereof. Among them, 10 fibers are arbitrarily selected, and a fiber diameter is directly read by drawing a line orthogonal to a longitudinal direction of the fiber, and thus, the thickness of the fiber can be measured.

In addition, the length of the fiber that forms the film is an unlimited length on the manufacturing principle, but in actuality, it is preferable to have a length of at least greater than or equal to 100 times the thickness of the fiber. For example, the film to be formed contains a fiber preferably having a length of greater than or equal to 10 μm, more preferably having a length of greater than or equal to 50 μm, and even more preferably having a length of greater than or equal to 100 μm.

Next, the nozzle 2B will be described. As illustrated in FIG. 3, the nozzle 2B includes an outer shell portion 22, a passage portion 23, and the tip portion 24. An outer surface 220 of the outer shell portion 22 is connected to a planar portion 201 on the nozzle 2B side of the outer surface of the cartridge side housing 20. The tip portion 24 supports the passage portion 23 on the inner surface side of the nozzle 2B. The passage portion 23 is a tubular portion inside the nozzle 2B. A linear passage 230 is provided on the inner circumference of the passage portion 23. The spray port 240 is opened in the tip portion 24. The spray port 240 is connected to the passage 230. An axis 9 of the nozzle 2B extends along the passage 230. A direction along the axis 9 of the nozzle 2B can be regarded as a direction in which the liquid is sprayed from the nozzle 2B, that is, a spray direction of the liquid.

The passage 230 is in a tapered shape in which the diameter gradually decreases toward the tip portion 24. Accordingly, a flow path is narrowed toward the tip portion 24, and thus, a spray velocity of the liquid from the spray port 240 increases, and the liquid or the like more intensively reaches the target. The outer surface 220 of the outer shell portion 22 is in a tapered shape in which the diameter decreases toward the tip portion 24.

Next, the first electrode member 5 will be described. The first electrode member 5 is formed of a conductive material and functions as an electrode to which a voltage can be applied from the high-voltage generator. Herein, the conductive material indicates a substance having volume specific resistivity, for example, of less than or equal to $10^4$ [Ω·cm], preferably less than or equal to $10^2$ [Ω·cm]. For example, a conductive resin in which carbon is blended or a metal material can be used as the conductive material. The first electrode member 5 includes a first bottom portion 51, a first wall portion 52, a needle-shaped electrode 53, a container connection portion 54, and the terminal 55. The needle-shaped electrode 53 functions as a base electrode. The first bottom portion 51 is in the shape of a plate that expands in a direction orthogonal to the axis 9 of the nozzle 2B. The first wall portion 52 is in the shape of a plate and protrudes toward the nozzle 2B side from the outer circumference side of the first bottom portion 51.

The needle-shaped electrode 53 is in the shape of a needle or a pin and protrudes toward the nozzle 2B side from the first bottom portion 51. The needle-shaped electrode 53 extends in the direction along the axis 9 of the nozzle 2B, that is, in a direction along the passage 230 inside the nozzle 2B. An axis of the needle-shaped electrode 53 is coincident or overlaps with the axis 9 of the nozzle 2B. The needle-shaped electrode 53 is in a tapered shape and has a diameter that decreases toward the nozzle 2B side. A tip 530 of the needle-shaped electrode 53 faces the spray target. A tip portion of the needle-shaped electrode 53 including the tip 530 is in a linear shape and is provided inside the passage 230.

The container connection portion 54 is in a cylindrical shape and protrudes toward a side opposite to the nozzle 2B from the first bottom portion 51. The spout of the container is connected to the container connection portion 54. A passage 540 is provided on the inner circumference of the container connection portion 54. The passage 540 is connected to the inside of the container. The terminal 55 is in the shape of a needle or a pin and protrudes toward a side opposite to the nozzle 2B from the first bottom portion 51.

Next, the second electrode member 3 will be described. The second electrode member 3 is formed of a conductive material and functions as an electrode to which a voltage can be applied from the high-voltage generator. The second electrode member 3 includes a second wall portion 31, a second bottom portion 32, and a tubular electrode 33. The second bottom portion 32 is in the shape of a plate that expands in the direction orthogonal to the axis 9 of the nozzle 2B and functions as an additional electrode. The second wall portion 31 is in the shape of a plate and protrudes toward a side opposite to the nozzle 2B from the outer circumference side of the second bottom portion 32. The first wall portion 52 of the of the first electrode member 5 is fitted into the inner circumference of the second wall portion 31. Accordingly, the first electrode member 5 and the second electrode member 3 are in contact with each other and are electrically connected to each other.

The tubular electrode 33 is in a cylindrical shape or in the shape of a cylinder and protrudes toward the nozzle 2B side from the second bottom portion 32. An axis of the tubular electrode 33 is coincident or overlaps with the axis 9 of the nozzle 2B. The tubular electrode 33 includes an inside portion 331 and an outside portion 332. An end portion of the passage portion 23 of the nozzle 2B on a side opposite to a side that is supported by the tip portion 24 is fitted into the inner circumference of the inside portion 331. The outside portion 332 is fitted into a cylindrical portion that is connected to the inner circumference surface of the outer shell portion 22 of the nozzle 2B in the containing recess 200.

Next, a positional relationship of each part will be described. The needle-shaped electrode 53 of the first electrode member 5 is disposed to extend along the axis of the tubular electrode 33. The needle-shaped electrode 53 is disposed on the second bottom portion 32 side of the second electrode member 3 from the tip portion 24 of the nozzle 2B, more specifically, on the first bottom portion 51 side of the first electrode member 5. In addition, the needle-shaped electrode 53 protrudes to the spray port 240 side with respect to the second bottom portion 32. The tip portion of the needle-shaped electrode 53 that is continuous to the tip 530 is on the inner circumference side of the inside portion 331 of the tubular electrode 33. The tip 530, the end of the inside portion 331 on the nozzle 2B side, and the end of the outside portion 332 on the nozzle 2B side have approximately the same height with respect to the second bottom portion 32.

Next, the pump 8 will be described. The pump 8 includes a pump cover 4, a driving gear 81, and a driven gear 82 (refer to FIG. 6). As illustrated in FIG. 3, the pump cover 4 is formed of an insulating material, and includes a plate-shaped main body portion and a tubular portion 40 that protrudes to the nozzle 2B side from the main body portion. A passage 400 is provided on the inner circumference of the tubular portion 40. The pump cover 4 is provided in the second bottom portion 32 of the second electrode member 3. The outer circumference side of the pump cover 4 is retained by being interposed between the second bottom portion 32 and the first wall portion 52 of the first electrode member 5. The passage 400 is connected to the passage 230 of the nozzle 2B and functions as a part of the passage 230. The needle-shaped electrode 53 passes through the passage 400.

Figure 6:
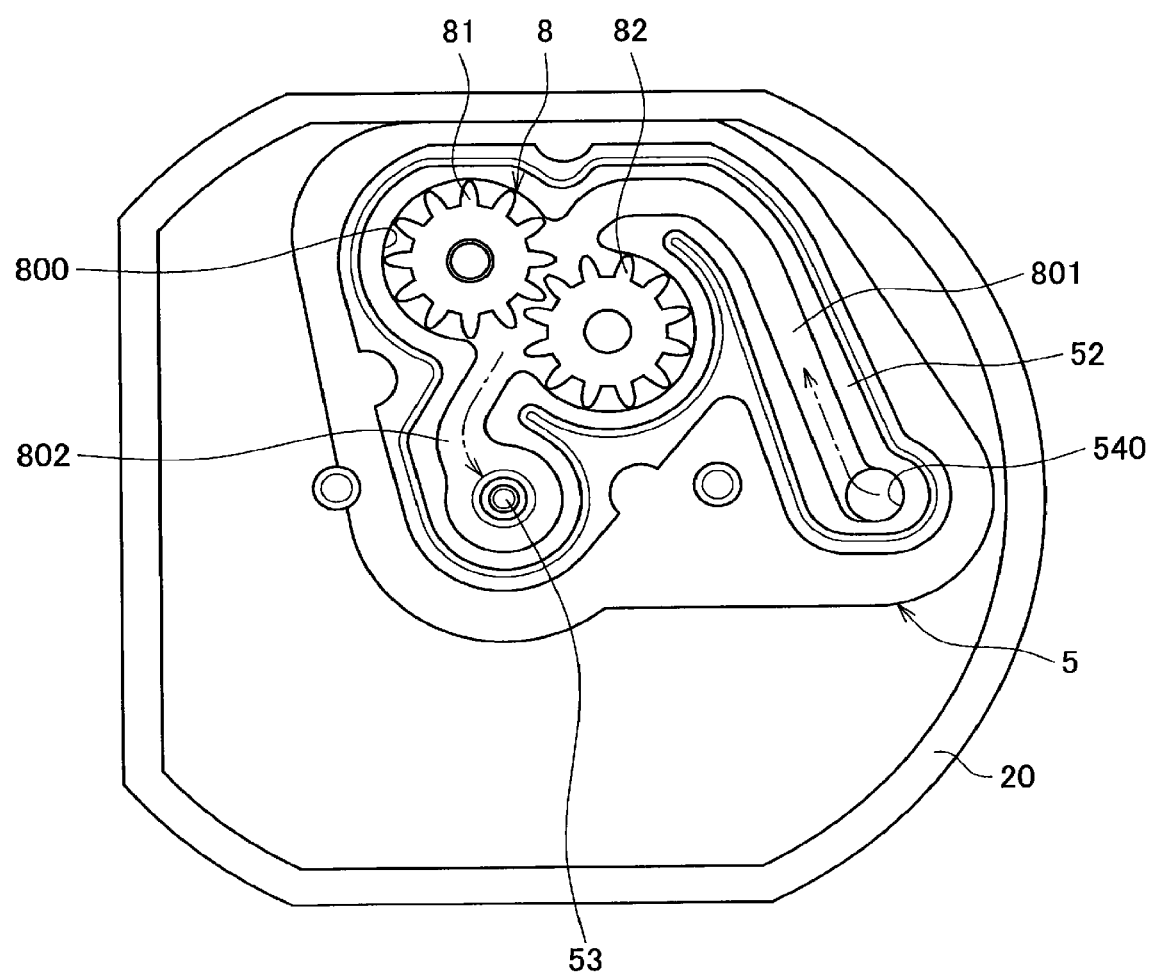
FIG. 6 is a front view of the cartridge of the electrostatic spray device according to the same embodiment from which a part of the housing, a first electrode member, and a pump cover are omitted.

A pump containing chamber 80 is formed by being surrounded by the pump cover 4, and the first bottom portion 51 and the first wall portion 52 of the first electrode member 5. As illustrated in FIG. 6, the pump containing chamber 80 includes a gear containing portion 800, a suction passage 801, and an ejection passage 802. One end of the suction passage 801 is connected to the passage 540 of the container connection portion 54, and the other end of the suction passage 801 is connected to the gear containing portion 800. One end of the ejection passage 802 is connected to the gear containing portion 800, and the other end of the ejection passage 802 is connected to the passage 400 (refer to FIG. 3). The driving gear 81 and the driven gear 82 are rotatably contained in the gear containing portion 800 and are engaged with each other. As illustrated by an arrow of a dashed-dotted line in FIG. 6, the liquid is sucked from the passage 540, and the liquid is ejected toward the passage 400, in accordance with the rotation of both of the gears 81 and 82.

Next, the first conductor 6 will be described. The first conductor 6 is a thin film-shaped member formed of a conductive material and is disposed on the circumference of the nozzle 2B on the outer surface of the cartridge side housing 20. The portion 201 surrounding the nozzle 2B on the outer surface of the cartridge side housing 20 is in the shape of a flat surface that is orthogonal to the axis 9 of the nozzle 2B. The first conductor 6 covers the portion 201. The first conductor 6 includes a surface that expands along a radial direction with respect to the axis 9 of the nozzle 2B. The first conductor 6 extends in a circumference direction of the axis 9 of the nozzle 2B. The first conductor 6 is in the shape of a ring that is connected over the entire range in the circumference direction of the axis 9. Note that, at least a part of the first conductor 6 may be disposed along the circumference of the axis 9, or the first conductor 6 may be in the shape of a ring in which a part thereof is disconnected.

Examples of the conductive material for forming the first conductor 6 include a metal such as aluminum and stainless steel and a mixed material of a metal and a synthetic resin. It is preferable that the thickness of the first conductor 6 is greater than or equal to 0.1 mm and less than or equal to 5 mm.

Figure 4:
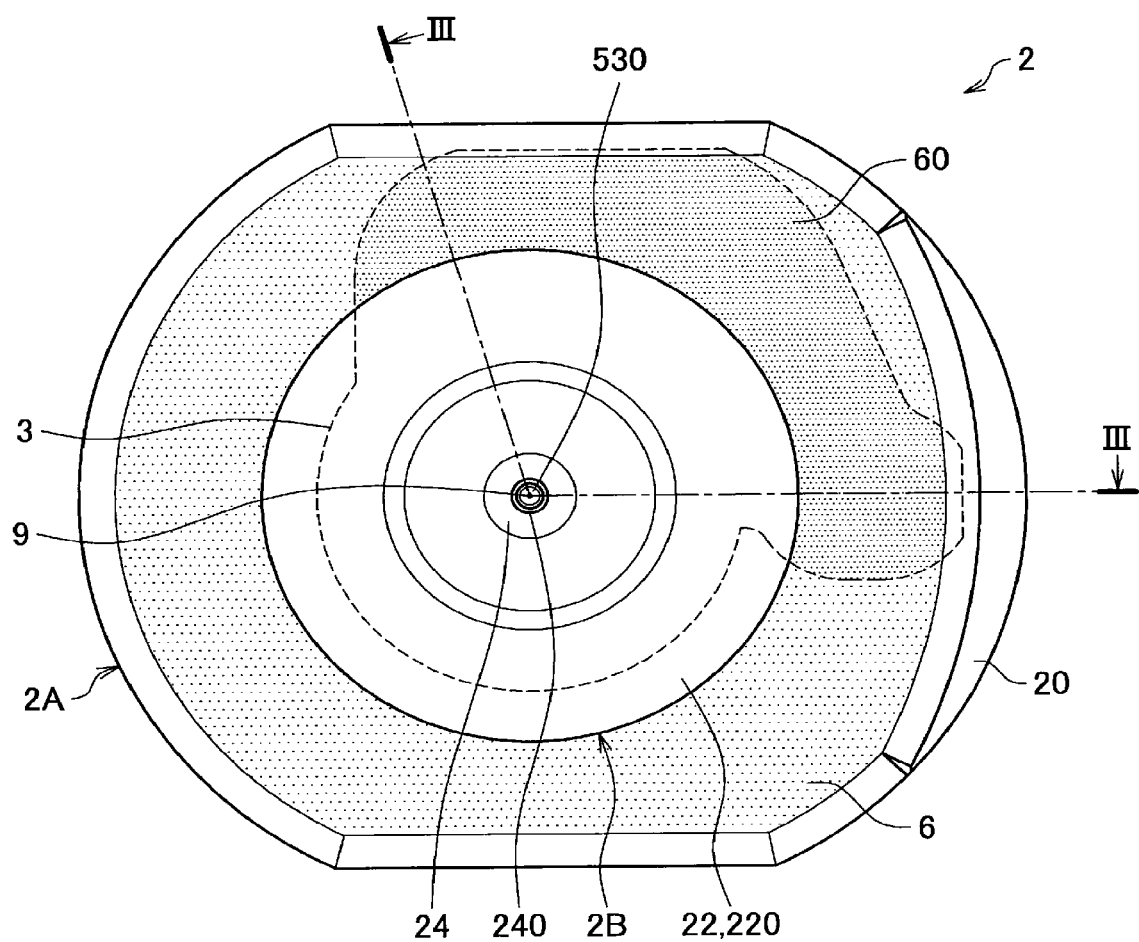
FIG. 4 is a front view of the cartridge of the electrostatic spray device according to the first embodiment of the present invention.
Figure 5:
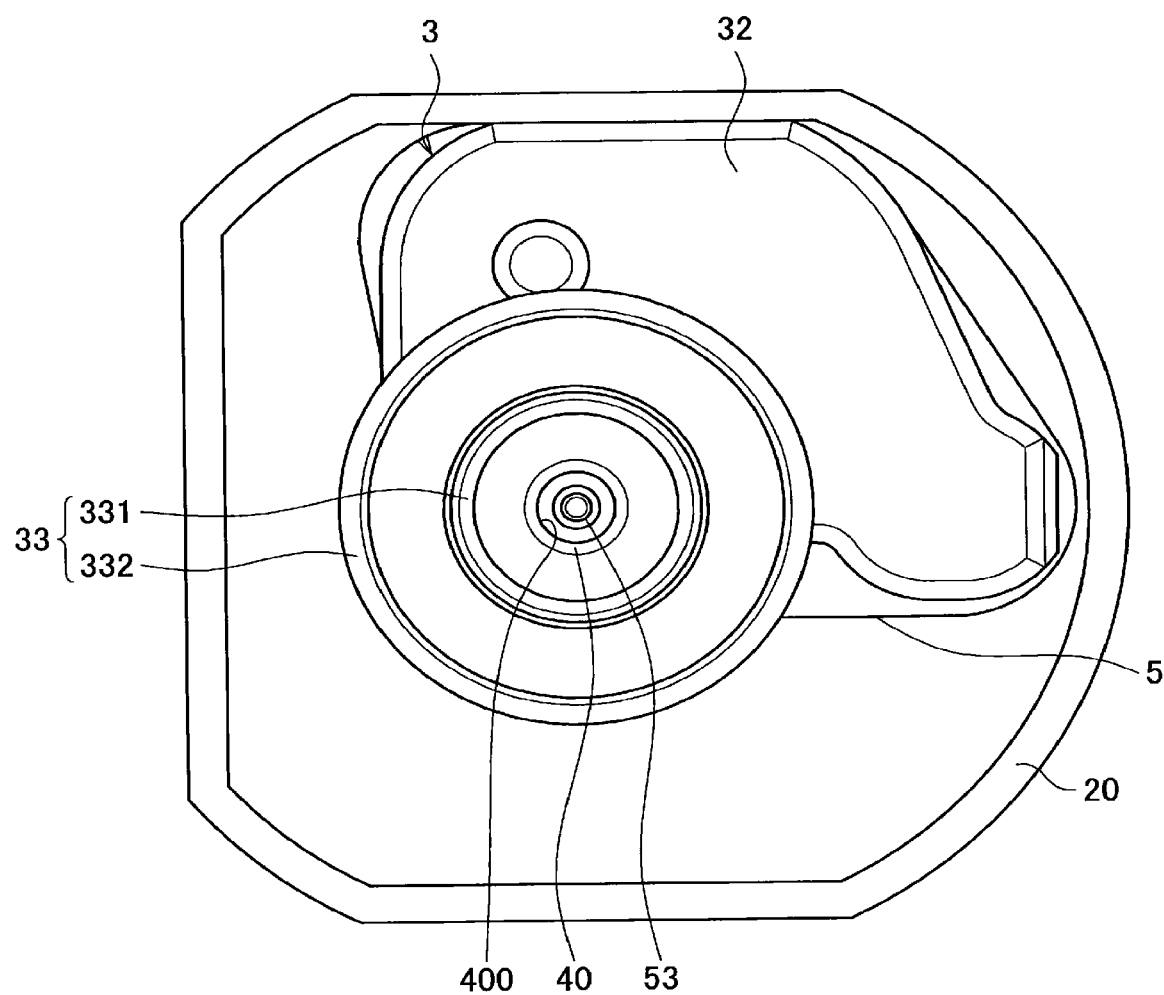
FIG. 5 is a front view of the cartridge of the electrostatic spray device according to the same embodiment from which a part of a housing is omitted.

Specifically, as illustrated in FIG. 4, the inner edge of the first conductor 6 is in a circular shape. As illustrated in FIG. 3, the inner edge of the first conductor 6 is in a position separated from the outside portion 332 of the tubular electrode 33, in the radial direction with respect to the axis 9 of the nozzle 2B. As it is obvious from FIGS. 4 and 5, the inner edge of the first conductor 6 extends in a direction along the outer circumference surface of the outside portion 332. At least a part 60 (refer to FIG. 4) of the first conductor 6 (the conductor) overlaps with the second bottom portion 32 (the additional electrode) of the second electrode member 3 in the radial direction with respect to the axis 9 of the nozzle 2B (a direction orthogonal to the spray direction of the liquid), in other words, when seen in the direction along the axis 9. Note that, the entire first conductor 6 may be configured to overlap with the second bottom portion 32 of the second electrode member 3, in the radial direction with respect to the axis 9 of the nozzle 2B.

As illustrated in FIG. 3, the first conductor 6 is interposed between the portion 201 on the outer surface of the cartridge side housing 20 and a circumference portion of the hole 100 on the inner surface 102 of the cover 10. The first conductor 6 is supported on the cartridge side housing 20 that is the insulator, and is electrically isolated from the electrode members 3 and 5 inside the cartridge side housing 20, that is, the high-voltage generator side.

The first conductor 6 is disposed on the nozzle 2B side or the tip 530 side of the needle-shaped electrode 53 from the second bottom portion 32 of the second electrode member 3 and is disposed slightly on the second bottom portion 32 side from the tip 530 of the needle-shaped electrode 53 in the direction along the axis 9 of the nozzle 2B. Note that, the first conductor 6 may be disposed in a position overlapping with the tip 530 in the direction along the axis 9, in other words, when seen in the radial direction with respect to the axis 9. The first conductor 6 is disposed slightly on the second bottom portion 32 side from the tip of the outside portion 332 of the tubular electrode 33 of the second electrode member 3 in the direction along the axis 9. Note that, the first conductor 6 may be disposed in a position overlapping with the tip of the outside portion 332 in the direction along the axis 9.

Next, the operation or the advantage of the device 1 according to this embodiment will be described. For example, a positive high voltage is applied to the needle-shaped electrode 53 of the first electrode member 5 and the tubular electrode 33 of the second electrode member 3 from the high-voltage generator through the terminal 55 or the like. An electric field with a high potential difference can be generated between the needle-shaped electrode 53 and the tubular electrode 33 (a positive potential), and the target (a ground potential) such as the skin facing the electrodes. It can be considered that, for example, the positively charged liquid progresses along an electric force line orthogonal to an equipotential surface in such an electric field. In a case where the liquid is the liquid composition, it can be considered that a fibrous solute progresses along a direction along the electric force line.

The needle-shaped electrode 53 is in contact with the liquid toward the spray port 240 of the nozzle 2B through the passages 400 and 230 and functions as an electrode for imparting an electric charge to the liquid to be electrically charged. The needle-shaped electrode 53 is provided to extend in the direction along the passage 230 of the liquid inside the nozzle 2B. Accordingly, the outer circumference surface of the needle-shaped electrode 53 is in contact with the liquid, and thus, the liquid can be efficiently electrically charged. Note that, the needle-shaped electrode 53 corresponds to a base electrode described in the claims. The base electrode may be an electrode to which a voltage is applied from the voltage source, may include the linear tip portion, and may have a function of electrically charging the liquid, and the shape or the dimension thereof is not limited to the shape or the dimension of the needle-shaped electrode 53.

The tip portion of the needle-shaped electrode 53 is inside the passage 230 with respect to the spray port 240 of the nozzle 2B. Accordingly, the tip 530 of the needle-shaped electrode 53 can be prevented from being in contact with the user, and thus, the protection of the user can be ensured. In addition, the tip 530 of the needle-shaped electrode 53 is inside the passage 230, and thus, the surface area of the liquid rising to the target side from the spray port 240 by a Coulomb force or a surface tension decreases, and thus, an electric charge is concentrated on the rising portion. Accordingly, the straightness of the liquid or the fibrous solute (hereinafter, referred to as the liquid or the like) to be sprayed is improved.

The tubular electrode 33 is disposed along the circumference of the axis 9 of the nozzle 2B, and a voltage is applied from the high-voltage generator. The tubular electrode 33 adjusts the state of the electric field in the vicinity of the tip 530 of the needle-shaped electrode 53 and functions as an electrode for suppressing, for example, corona discharge. In addition, the sign (positive) of the electric charge of the tubular electrode 33 is the same as the sign (positive) of the electric charge of the needle-shaped electrode 53. Accordingly, the liquid to be sprayed is prevented from being dispersed by spreading to the outside of the radial direction with respect to the axis 9 of the nozzle 2B, in the vicinity of the tip 530 of the needle-shaped electrode 53, specifically, in the spray port 240 of the nozzle 2B. Accordingly, the straightness of the liquid or the like is improved. Accordingly, a spray range of the liquid or the like in the target can be further concentrated. The tubular electrode 33 is in a tubular shape surrounding the tip portion of the needle-shaped electrode 53. Accordingly, the state of the electric field in the vicinity of the tip 530 can be more effectively adjusted. Note that, the tubular electrode 33 is not limited to a cylindrical shape, and the cross-section thereof orthogonal to the axis may be in an elliptical shape, a polygonal shape, or the like.

At least a part of the first bottom portion 51 of the first electrode member 5 configures the pump containing chamber 80. Accordingly, the number of parts can be reduced, and the device 1 can be compactified. The container connection portion 54 and the first bottom portion 51 of the first electrode member 5 configure a liquid passage from the container to the needle-shaped electrode 53 and function as an electrode for electrically charging the liquid by being in contact with the liquid flowing through the passage. Accordingly, an electric charge can be efficiently accumulated in the liquid, and the generation of a current in the liquid can be suppressed. In addition, the first bottom portion 51 is electrically connected to the second wall portion 31 of the second electrode member 3 and also functions as a conducting body for supplying a voltage to the second electrode member 3 side from the terminal 55 side.

The second wall portion 31 and the second bottom portion 32 of the second electrode member 3 are electrically connected to the tubular electrode 33 and function as a conducting body for supplying a voltage to the tubular electrode 33 from the terminal 55 side. Note that, the second bottom portion 32 corresponds to an additional electrode described in the claims. The additional electrode may be an electrode to which a voltage is applied from the voltage source, and the shape or the dimension thereof is not limited to the shape or the dimension of the second bottom portion 32.

The tip 530 of the needle-shaped electrode 53 is disposed on the spray side of the liquid from the second bottom portion 32 of the second electrode member 3, that is, the target side. Accordingly, the influence of the electric field due to the second bottom portion 32 is suppressed on the tip 530 side, and thus, it is easy for the needle-shaped electrode 53 to more intensively impart an electric charge to the liquid.

The first conductor 6 is disposed on the spray side of the liquid from the second bottom portion 32 (the additional electrode) of the second electrode member 3, that is, the target side. Accordingly, the straightness of the liquid or the like to be sprayed can be improved.

That is, the first conductor 6 is adjacent to the second bottom portion 32. The second bottom portion 32 is electrically charged, and thus, the surface of the first conductor 6 is electrically charged by electrostatic induction, and therefore, is capable of having a comparatively high potential. For example, in the first conductor 6, the surface of a portion adjacent to the second bottom portion 32 is electrically charged by an electric charge of a sign (for example, negative) opposite to that of the second bottom portion 32, and the surface on a side opposite to the portion is electrically charged by an electric charge of a sign (positive) identical to that of the second bottom portion 32. The first conductor 6 is on the spray side of the liquid from the second bottom portion 32, that is, the target side. Accordingly, the sign (positive) of the electric charge to be induced to the surface of the first conductor 6 facing the target is identical to a sign (positive) that is identical to that of the electric charge of the second bottom portion 32, that is, the sign (positive) of the electric charge of the needle-shaped electrode 53 facing the target.

Accordingly, the liquid to be sprayed is prevented from being dispersed by spreading to the outside of the radial direction with respect to the axis 9 of the nozzle 2B, in the vicinity of the tip 530 of the needle-shaped electrode 53, specifically, in the spray port 240 of the nozzle 2B, and thus, the straightness of the liquid or the like is improved. In particular, this is effective in a high humidity environment. In addition, the surface of the first conductor 6 facing the target is electrically charged, and thus, an electric field from the needle-shaped electrode 53 to the target is ordered as a whole, and the electric force line is concentrated on a narrower range of the target. Accordingly, the straightness of the liquid or the like is also improved. As described above, the straightness is improved, and the spreading range of the liquid or the like is narrowed, and thus, when a distance between the device 1 and the target is short, the spray range in the target decreases, and the density increases. In a case where the device 1 is the electrostatic spinning device, the adhesiveness or the homogeneousness of the film to be formed is improved. When the distance is long, the liquid or the like reaches further. In a case where the device 1 is the electrostatic spinning device, the fiber to be formed efficiently reaches the target.

At least a part 60 of the first conductor 6 (the conductor) overlaps with the second bottom portion 32 (the additional electrode) in the direction orthogonal to the spray direction of the liquid, for example, the radial direction with respect to the axis of the nozzle 2B. In other words, a part 60 of the first conductor 6 and the second bottom portion 32 are disposed to overlap with each other when seen from the tip 530 side of the needle-shaped electrode 53. Accordingly, an electric charge can be efficiently induced to the surfaces of the first conductor 6 on both sides in the spray direction of the liquid by the second bottom portion 32. For this reason, the advantage of the first conductor 6 can be effectively obtained.

At least a part of the second bottom portion 32 of the second electrode member 3 includes a surface expanding along the direction orthogonal to the spray direction of the liquid, for example, the radial direction with respect to the axis 9 of the nozzle 2B. Accordingly, it is easy for the second electrode member 3 to form the pump containing chamber 80 together with the first electrode member 5. In addition, it is easy to increase a region in which the second bottom portion 32 overlaps with the first conductor 6, in the direction orthogonal to the spray direction of the liquid, in other words, when seen in the direction along the spray direction of the liquid, and an electric charge can be efficiently induced to the first conductor 6 by the second bottom portion 32. For this reason, the advantage of the first conductor 6 can be effectively obtained.

At least a part of the first conductor 6 includes a surface expanding along the direction orthogonal to the spray direction of the liquid, for example, the radial direction with respect to the axis 9 of the nozzle 2B. Accordingly, the area of the surface of the first conductor 6 that is electrically charged and faces the target can be increased, and thus, the function of the first conductor 6 can be improved in which the electric field from the needle-shaped electrode 53 to the target is ordered as a whole.

At least a part of the first conductor 6 is disposed along the circumference of the tip portion of the needle-shaped electrode 53 (the base electrode), for example, the circumference of the axis 9 of the nozzle 2B. Accordingly, the range of the electrically charged first conductor 6 in the circumference direction of the tip portion, in other words, the range of the first conductor 6 facing the tip portion of the needle-shaped electrode 53 can be increased. For this reason, the liquid to be sprayed is prevented from spreading to the outside of the radial direction with respect to the axis 9 of the nozzle 2B, and the function of the first conductor 6 can be improved in which the electric field from the needle-shaped electrode 53 to the target is ordered. From such a viewpoint, it is preferable that the first conductor 6 is disposed in a range of greater than or equal to 180 degrees in the circumference direction of the tip portion of the needle-shaped electrode 53. The first conductor 6 of this embodiment is in the shape of a ring surrounding the tip portion of the needle-shaped electrode 53. More specifically, the first conductor 6 is in the shape of a ring that is connected over the entire range in the circumference direction of the tip portion of the needle-shaped electrode 53. Accordingly, the electric charge of the first conductor 6 is distributed over the entire range surrounding the tip portion, and thus, the function of the first conductor 6 can be further improved. For example, the electric field from the device 1 to the target is further ordered, and it is easy to further concentrate the spray range in the target.

The device 1 is the hand-held type device, and one device 1 includes one nozzle 2B. Accordingly, there are no other nozzles adjacent to the nozzle 2B in a direction along an outer surface 101 to which the nozzle 2B of the device 1 protrudes. In other words, there are no other first conductors 6 adjacent to the first conductor 6 provided corresponding to the nozzle 2B in the direction orthogonal to the axis 9 of the nozzle 2B. Accordingly, interference in electric fields that are respectively formed by a plurality of first conductors 6 can be avoided.

The first conductor 6 is disposed on the second bottom portion 32 side of the second electrode member 3 from the tip portion 24 of the nozzle 2B, in other words, on a side opposite to the target. Accordingly, interference between the liquid or the like to be sprayed from the nozzle 2B and the first conductor 6 can be suppressed. In addition, an increase in the distance between the first conductor 6 and the second bottom portion 32 is suppressed in the spray direction of the liquid, for example, the direction along the axis 9 of the nozzle 2B. For this reason, an electric charge can be efficiently induced to the surface of the first conductor 6 by the second bottom portion 32.

More specifically, the first conductor 6 may be disposed in the position overlapping with the tip 530 of the needle-shaped electrode 53 or on the second bottom portion 32 side from the tip 530, in the spray direction of the liquid, for example, the direction along the axis 9 of the nozzle 2B. Accordingly, the function of the needle-shaped electrode 53 for forming the electric field can be prevented from being weakened by the electric charge of the first conductor 6. In addition, an increase in the distance between the first conductor 6 and the second bottom portion 32 is further suppressed in the spray direction of the liquid, and thus, an electric charge can be more efficiently induced to the surface of the first conductor 6 by the second bottom portion 32. Note that, the first conductor 6 may be disposed on a side away from the second bottom portion 32 to some extent from the tip 530 of the needle-shaped electrode 53, that is, on the tip portion 24 side of the nozzle 2B, unless the function of the needle-shaped electrode 53 for forming the electric field is significantly weakened.

The first conductor 6 is disposed along the circumference of the tubular electrode 33. Accordingly, the induction of the electric charge on the surface of the first conductor 6 can be accelerated by the tubular electrode 33. The inner edge of the first conductor 6 is on the outside of the radial direction with respect to the axis 9 of the nozzle 2B from the outside portion 332 of the tubular electrode 33. In other words, the first conductor 6 is disposed not to overlap with the tip of the tubular electrode 33 when seen from the tip side of the tubular electrode 33. Accordingly, the function of the first conductor 6 and the function of the tubular electrode 33 can be prevented from being weakened by interference therebetween. The first conductor 6 may be disposed in the position overlapping with the tip of the tubular electrode 33 or on the second bottom portion 32 side from the tip of the tubular electrode 33, in the direction along the axis of the tubular electrode 33. Accordingly, the induction of the electric charge on the surface of the first conductor 6 can be more effectively accelerated by the tubular electrode 33.

The first conductor 6 is electrically isolated from the second electrode member 3 and the first electrode member 5, specifically, the second bottom portion 32 (the additional electrode) and the needle-shaped electrode 53 (the base electrode), and is electrically charged by the electrostatic induction. Accordingly, the first conductor 6 does not have an excessively high voltage, and even in a case where a person touches the first conductor 6, a current does not continuously flow to the person from the first conductor 6, which is more advantageous. In particular, the device 1 is the hand-held type device and is hardly grounded, and thus, insulating properties with respect to the user can be improved, which is advantageous. In addition, in order to electrically charge the surface of the first conductor 6, it is not necessary to separately provide a conducting body connecting the first conductor 6 and the electrode members 3 and 5. For this reason, a layout freedom of the first conductor 6 is high, and the configuration of the device 1 can be simplified.

The first conductor 6 is disposed in the cartridge side housing 20 or the like that is formed of the insulating material, and thus, is supported by the insulator. Accordingly, the electric connection between the first conductor 6 and the electrode members 3 and 5 can be suppressed by the insulator, and thus, it is easy to more reliably electrically isolate the first conductor 6 from the electrode members 3 and 5. Note that, from such a viewpoint, a part of the first conductor 6 or the entire first conductor 6, for example, may be embedded in the insulator by insert molding.

In this embodiment, the insulator is the cartridge side housing 20. Specifically, the first conductor 6 is provided in the portion 201 on the outer surface of the cartridge side housing 20. Accordingly, the cartridge side housing 20 is interposed between the first conductor 6 and the electrode members 3 and 5, and thus, the electric connection between the first conductor 6 and the electrode members 3 and 5 can be suppressed. Note that, from such a viewpoint, a part of the first conductor 6 or the entire first conductor 6 may be embedded inside the cartridge side housing 20.

Second Embodiment

Figure 7:
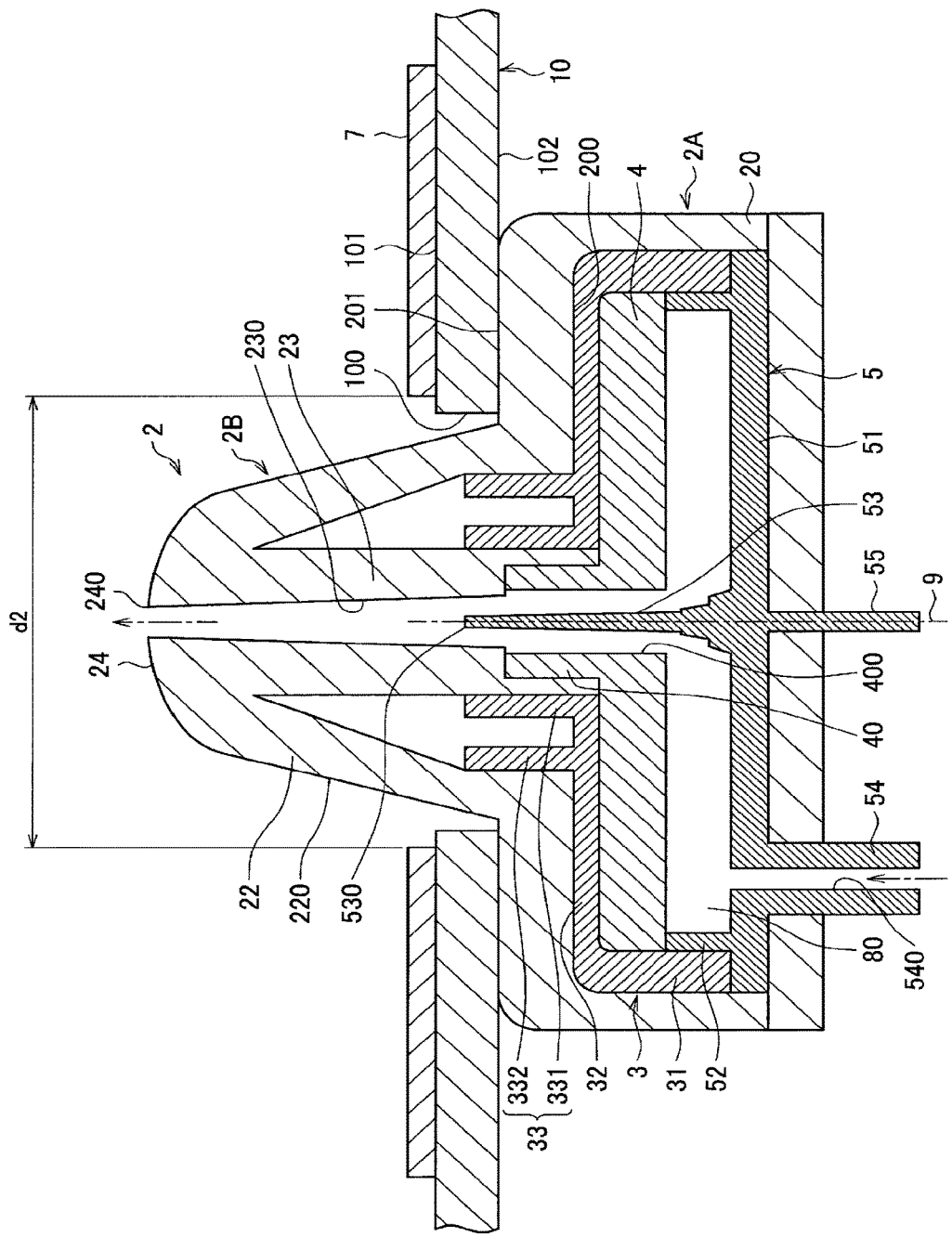
FIG. 7 is a sectional view of a part of a cover and a cartridge of an electrostatic spray device according to a second embodiment of the present invention.

Next, the electrostatic spray device 1 according to a second embodiment will be described with reference to FIGS. 7 and 8. The same reference numerals as those in the first embodiment will be applied to the configurations common to the first embodiment, and the description thereof will be omitted.

The first conductor 6 is not provided in the cartridge 2 of this embodiment. The device 1 of this embodiment includes a second conductor 7 on the outer surface 101 of the cover 10. The second conductor 7 is a thin film-shaped member that is formed of a conductive material and is provided in a circumference portion of the hole 100 on the outer surface 101 of the cover 10. The second conductor 7 includes a surface expanding along the radial direction with respect to the axis 9 of the nozzle 2B. Such a surface faces the spray target together with the nozzle 2B. The second conductor 7 extends in the circumference direction of the axis 9 of the nozzle 2B and surrounds the circumference of the hole 100. The second conductor 7 is in the shape of a ring that is connected over the entire range in the circumference direction of the axis 9. Note that, at least a part of the second conductor 7 may be disposed along the circumference of the axis 9, or the second conductor 7 may be in the shape of a ring in which a part thereof is disconnected.

Figure 8:
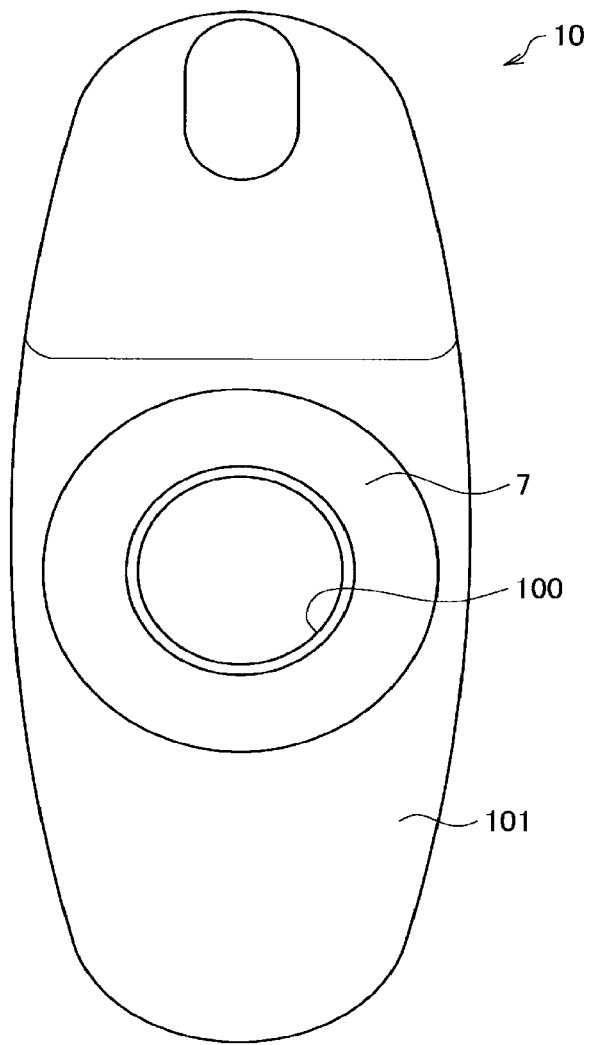
FIG. 8 is a front view of the cover of the electrostatic spray device according to the same embodiment.

Specifically, as illustrated in FIG. 8, both of the inner edge and the outer edge of the second conductor 7 are in a circular shape. As illustrated in FIG. 7, the inner edge of the second conductor 7 is in a position separated from the outside portion 332 of the tubular electrode 33 in the radial direction with respect to the axis 9 of the nozzle 2B. The inner edge of the second conductor 7 extends in the direction along the outer circumference surface of the outside portion 332. At least a part of the second conductor 7 (the conductor) overlaps with the second bottom portion 32 (the additional electrode) of the second electrode member 3 in the radial direction with respect to the axis 9 of the nozzle 2B (the direction orthogonal to the spray direction of the liquid), in other words, when seen in the direction along the axis 9. The second conductor 7 is disposed on the tip portion 24 side of the nozzle 2B from the tip 530 of the needle-shaped electrode 53 and the tip of the tubular electrode 33 in the direction along the axis 9. Note that, the entire second conductor 7 may be configured to overlap with the second bottom portion 32 of the second electrode member 3 in the radial direction with respect to the axis 9 of the nozzle 2B.

As described above, the second conductor 7 is disposed on the spray side of the liquid from the second bottom portion 32, that is, the target side. Accordingly, as with the first conductor 6, the surface of the second conductor 7 is electrically charged by the electrostatic induction. The sign (positive) of the electric charge to be induced to the surface of the second conductor 7 facing the target is identical to a sign (positive) that is identical to that of the electric charge of the second bottom portion 32, that is, the sign (positive) of the electric charge of the needle-shaped electrode 53 facing the target. Accordingly, the straightness of the liquid or the like to be sprayed can be improved.

The second conductor 7 is supported on the cover 10 that is the insulator, and is electrically isolated from the electrode members 3 and 5 inside the cartridge side housing 20, that is, the high-voltage generator side. Specifically, the second conductor 7 is provided on the outer surface 101 of the cover 10. Accordingly, the cover 10 is interposed between the second conductor 7 and the electrode members 3 and 5, and thus, electric connection between the second conductor 7 and the electrode members 3 and 5 can be suppressed. Note that, from such a viewpoint, a part of the second conductor 7 or the entire second conductor 7 may be embedded inside the cover 10. In this case, the hand of the user can be prevented from being in contact with the second conductor 7 insofar as the second conductor 7 is embedded not to be exposed to the outer surface 101 of the cover 10. Accordingly, the electric charge of the second conductor 7 can be prevented from being leaked to the hand of the user, and thus, the function of the second conductor 7 can be prevented from being impaired. Note that, the surface of the second conductor 7 facing the target may be covered with an insulator other than the cover 10.

The second conductor 7 is provided on the cover 10, and thus, a freedom degree of the size or the shape of the surface of the second conductor 7 is high. Accordingly, the electric field from the device 1 to the target can be more finely adjusted. For example, the second conductor 7 can be provided to the outside from the outer edge of the cartridge side housing 20 in the radial direction with respect to the axis 9 of the nozzle 2B.

In addition, the same advantage as the advantage of the first conductor 6 can be obtained by the configuration of the second conductor 7 that is identical to that of the first conductor 6.

Third Embodiment

Next, the electrostatic spray device 1 according to a third embodiment will be described with reference to FIG. 3. The same reference numerals as those in the first embodiment will be applied to the configurations common to the first embodiment, and the description thereof will be omitted.

The first conductor 6 of this embodiment is placed on the inner surface 102 of the cover 10. That is, the first conductor 6 is supported on the cover 10 that is the insulator. The first conductor 6 is provided in the circumference portion of the hole 100 on the inner surface 102 of the cover 10.

As with the first embodiment, the cartridge side housing 20 that is the insulator is interposed between the first conductor 6 and the electrode members 3 and 5. Accordingly, the electric connection between the first conductor 6 and the electrode members 3 and 5 can be suppressed. Note that, from such a viewpoint, a part of the first conductor 6 or the entire first conductor 6 may be embedded inside the cover 10.

As with the second embodiment, the first conductor 6 is provided on the cover 10, and thus, a freedom degree of the size or the shape of the surface of the first conductor 6 is high. For example, the first conductor 6 can also be provided to the outside from the outer edge of the cartridge side housing 20 in the radial direction with respect to the axis 9 of the nozzle 2B.

Fourth Embodiment

Figure 9:
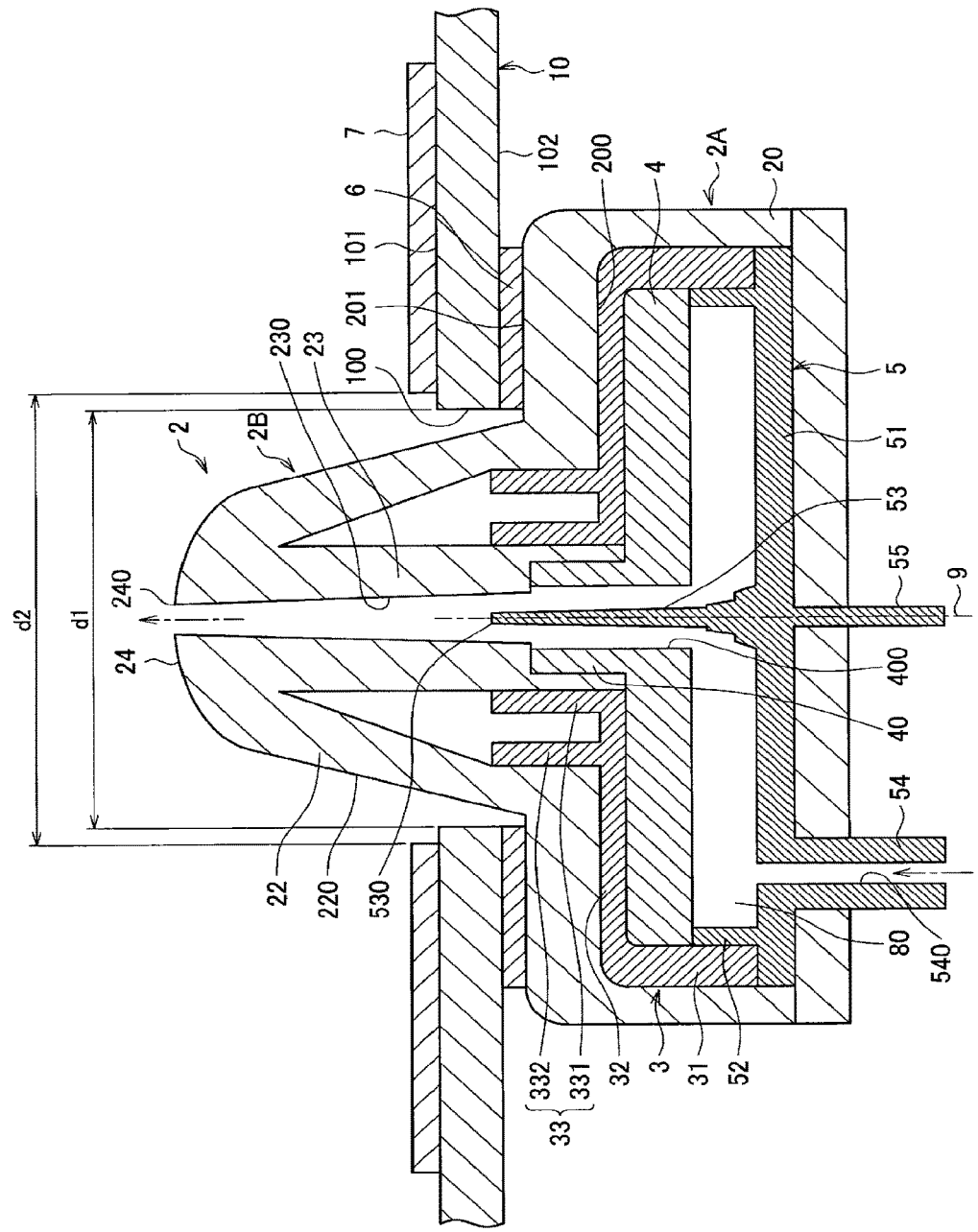
FIG. 9 is a sectional view of a part of a cover and a cartridge of an electrostatic spray device according to a fourth embodiment or a fifth embodiment of the present invention.

Next, the electrostatic spray device 1 according to a fourth embodiment will be described with reference to FIG. 9. The same reference numerals as those in the first embodiment will be applied to the configurations common to the first embodiment, and the description thereof will be omitted.

The device 1 of this embodiment includes the first conductor 6 and the second conductor 7. As with the second embodiment, the second conductor 7 is provided on the outer surface 101 of the cover 10. As with the first embodiment, the first conductor 6 is provided in the portion 201 on the outer surface of the cartridge side housing 20. Therefore, the first conductor 6 is positioned on the inner surface side, and the second conductor 7 is positioned on the outer surface side, with respect to the cover 10. The second conductor 7 is disposed on the tip portion 24 side of the nozzle 2B from the first conductor 6. A part of the second conductor 7 overlaps with the first conductor 6 in the radial direction with respect to the axis 9 of the nozzle 2B. The outer diameter of the second conductor 7 is formed to be larger than the outer diameter of the first conductor 6. In addition, an inner diameter (d1) of the inner edge of the first conductor 6 is formed to be smaller than an inner diameter (d2) of the inner edge of the second conductor 7.

As described above, the second conductor 7 is adjacent to the first conductor 6. As with the first embodiment, the surface of the first conductor 6 is electrically charged by the electrostatic induction. For this reason, the surface of the second conductor 7 is also successively electrically charged by the electrostatic induction. For example, in the second conductor 7, the surface of a portion adjacent to the first conductor 6 is electrically charged by an electric charge of a sign (negative) opposite to that of the adjacent surface of the first conductor 6, and the surface on a side opposite to the portion is electrically charged by an electric charge of a sign (positive) identical to that of the adjacent surface of the first conductor 6. The second conductor 7 is on the spray side of the liquid from the first conductor 6, that is, the target side. Accordingly, the sign (positive) of the electric charge to be induced to the surface of the second conductor 7 facing the target is identical to the sign (positive) of the electric charge of the needle-shaped electrode 53 facing the target. Therefore, the advantage of the first conductor 6 in the first embodiment and the advantage of the second conductor 7 in the second embodiment can be superimposingly obtained.

Note that, from such a viewpoint, the number of conductors is not limited to 2, and may be greater than or equal to 3. The outermost conductor is positioned closest to the target, and thus, the function of ordering the electric field from the needle-shaped electrode 53 to the target can be effectively exhibited. A conductor in a position between the outermost conductor and the second bottom portion 32 links the succession of the electrostatic induction as described above, and thus, an electric charge is induced to the surface of the outermost conductor. Accordingly, many electric charges can be more efficiently induced to the surface of the outermost conductor, compared to a case where such a conductor linking the succession of the electrostatic induction is not provided. In addition, in order to electrically charge the surface of the outermost conductor, it is not necessary to separately provide a conducting body connecting the conductor and the other conductor. For this reason, a layout freedom of the outermost conductor is high, and the configuration of the device 1 can be simplified.

The first conductor 6 and the second conductor 7 overlap with each other in the direction orthogonal to the spray direction of the liquid, for example, the radial direction with respect to the axis 9 of the nozzle 2B. In other words, both of the conductors 6 and 7 are disposed to at least partially overlap with each other when seen from the tip 530 side of the needle-shaped electrode 53. Accordingly, an electric charge can be efficiently induced to the surfaces of the second conductor 7 on both sides in the spray direction of the liquid, for example, the direction along the axis 9 of the nozzle 2B, by the first conductor 6.

The cover 10 that is the insulator is interposed between the first conductor 6 and the second conductor 7, and thus, the conductors 6 and 7 are electrically isolated from each other. Accordingly, the electrostatic induction in both of the conductors 6 and 7 can be smoothly attained, and an electric charge can be effectively induced to the surfaces of both of the conductors 6 and 7.

Fifth Embodiment

Next, the electrostatic spray device 1 according to a fifth embodiment will be described with reference to FIG. 9. The same reference numerals as those in the fourth embodiment will be applied to the configurations common to the fourth embodiment, and the description thereof will be omitted.

The first conductor 6 of this embodiment is identical to that of the third embodiment and is provided on the inner surface 102 of the cover 10.

Sixth Embodiment

Figure 10:
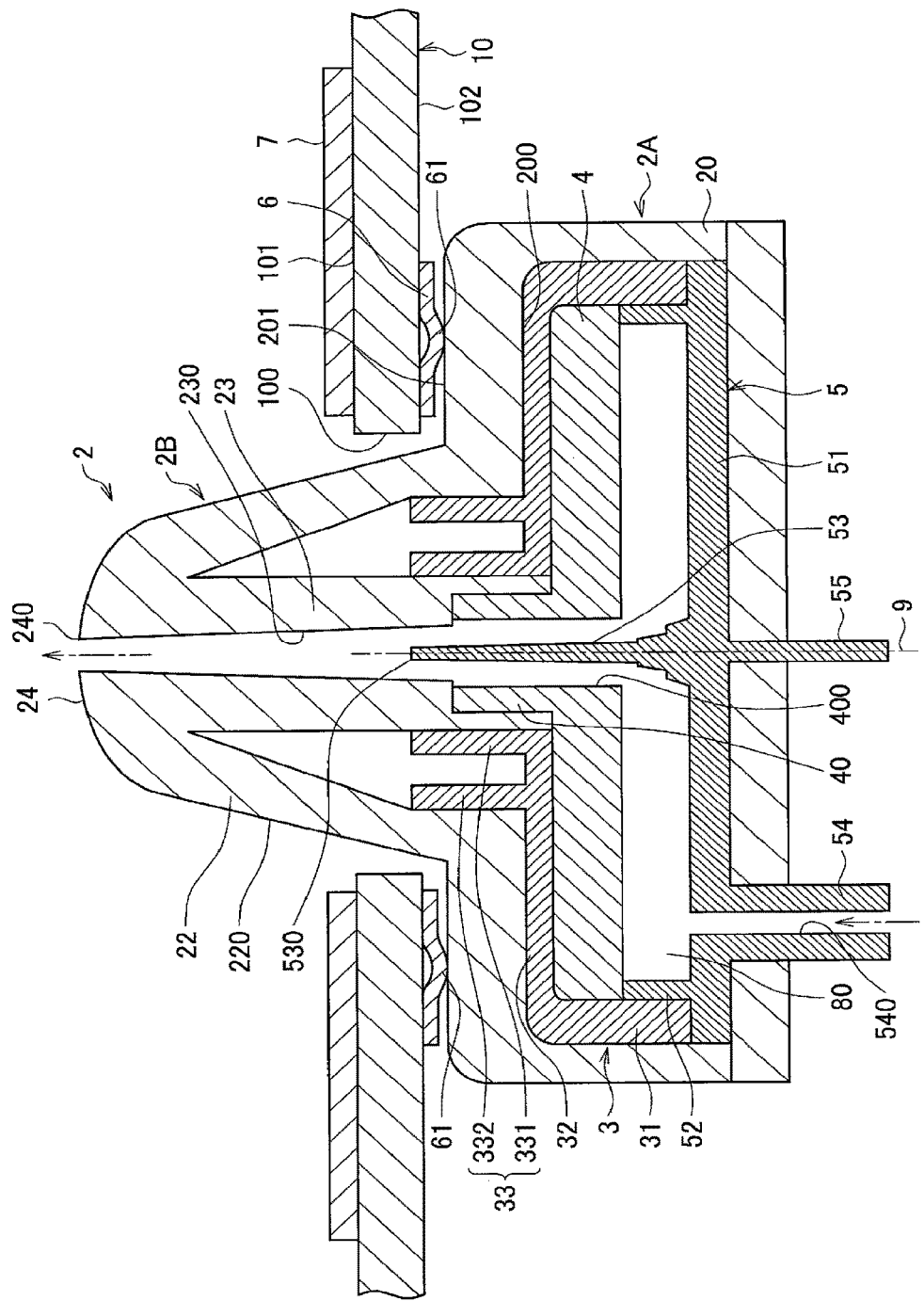
FIG. 10 is a sectional view of a part of a cover and a cartridge of an electrostatic spray device according to a sixth embodiment of the present invention.
Figure 11:
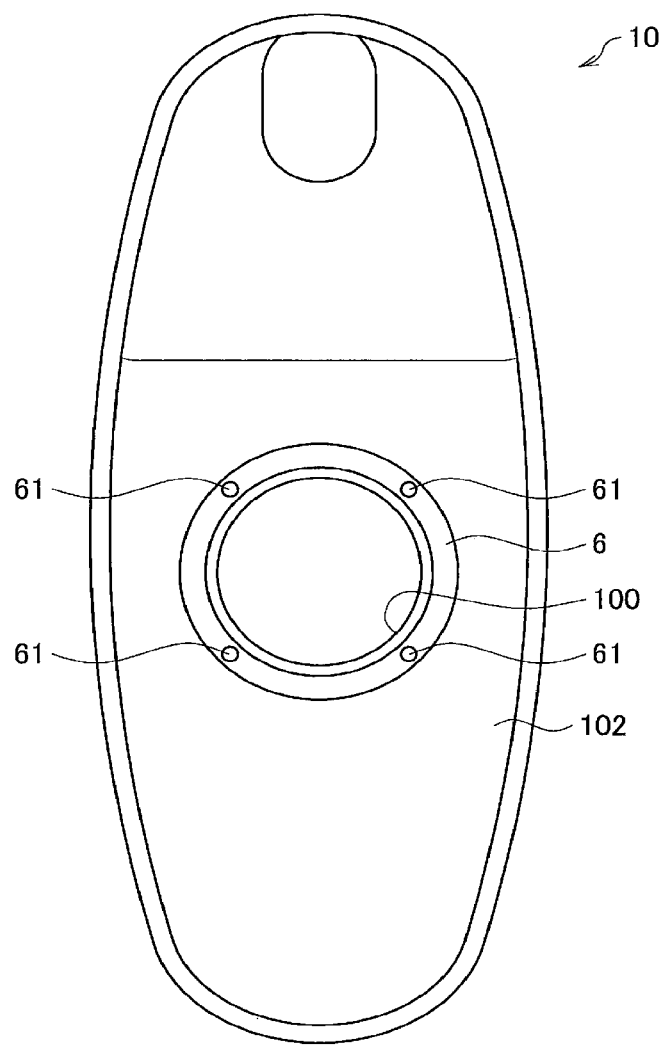
FIG. 11 is a rear view of the cover of the electrostatic spray device according to the same embodiment.

Next, the electrostatic spray device 1 according to a sixth embodiment will be described with reference to FIGS. 10 and 11. The same reference numerals as those in the fifth embodiment will be applied to the configurations common to the fifth embodiment, and the description thereof will be omitted.

The first conductor 6 of this embodiment is provided on the inner surface 102 of the cover 10. Four protrusions 61 are provided on the first conductor 6. Such protrusions 61 are disposed at regular intervals in a circumferential direction of the first conductor 6. Note that, in FIG. 10, a cross-section passing through the portion of the protrusion 61 in FIG. 11 is illustrated as the cross-section of the cover 10 including the first conductor 6. Each of the protrusions 61 is in the shape of a convex dome with respect to the surface of the first conductor 6 and protrudes toward the cartridge side housing 20 side from the inner surface 102 side of the cover 10. The protrusion 61 is formed of a conductive material integrally with the first conductor 6. In a case where the first conductor 6 is formed of a metal piece, the protrusion 61, for example, may be formed by press working.

The protrusion 61 abuts on the planar portion 201 on the outer surface of the cartridge side housing 20 and presses the mounting portion 2A of the cartridge 2 against the main body side housing 11. When the cover 10 is mounted on the main body side housing 11, at least a part of the plurality of protrusions 61 is capable of pressing the mounting portion 2A against the main body side housing 11 even in a case where there is some rattling. For this reason, the terminal 55 of the cartridge 2 can be more reliably connected to the output terminal of the high-voltage generator, or the driving shaft of the pump 8 can be more reliably connected to the output shaft of the motor. In addition, the protrusion 61 of the first conductor 6 is disposed close to the second bottom portion 32, and thus, an electric charge can be more reliably induced to the first conductor 6 through the protrusion 61. For this reason, the advantage of the first conductor 6 can be stably obtained. Note that, the number of protrusions 61 or the disposition thereof can be suitably changed.

Seventh Embodiment

Figure 12:
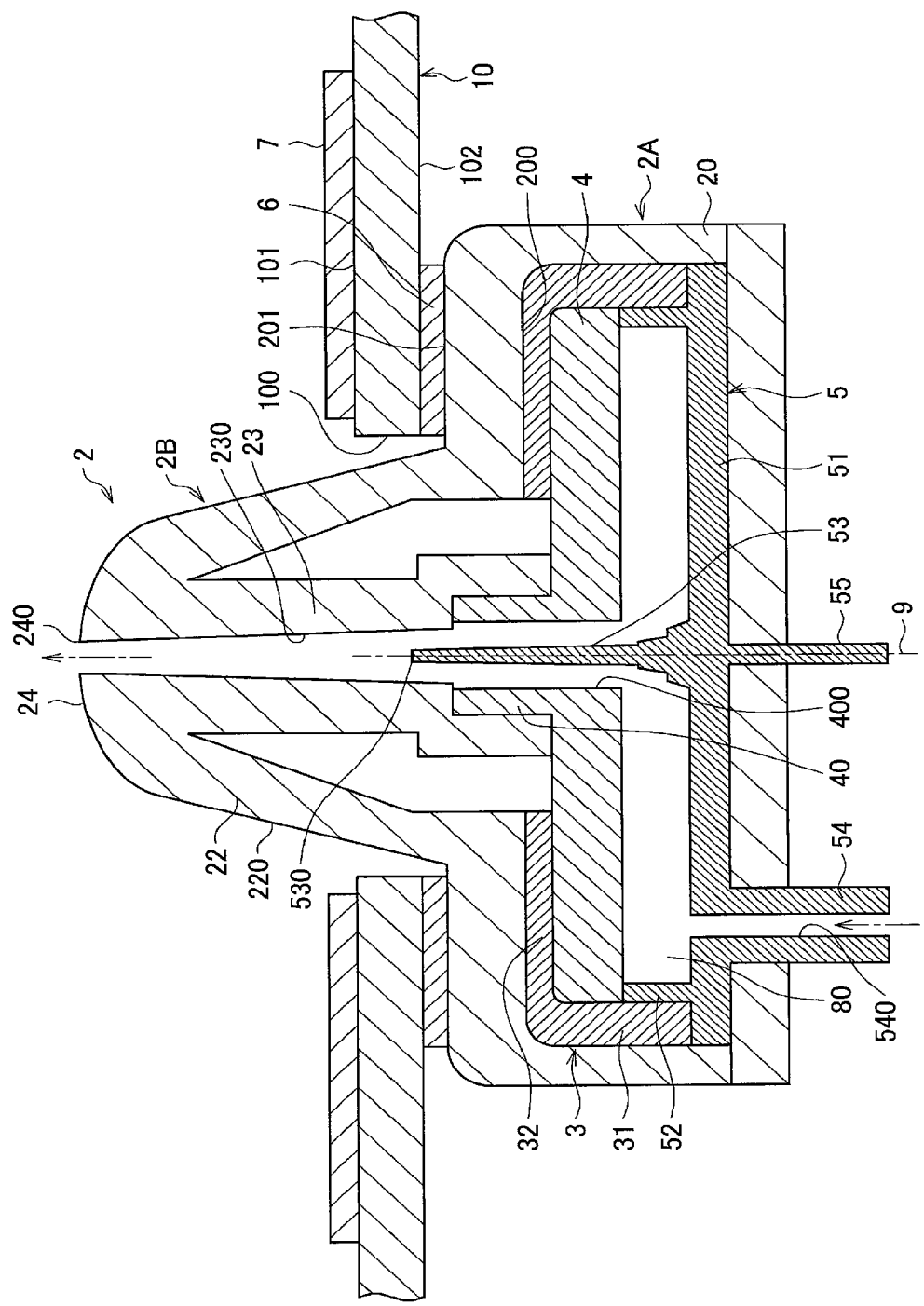
FIG. 12 is a sectional view of a part of a cover and a cartridge of an electrostatic spray device according to a seventh embodiment of the present invention.

Next, the electrostatic spray device 1 according to a seventh embodiment will be described with reference to FIG. 12. The same reference numerals as those in the fourth embodiment will be applied to the configurations common to the fourth embodiment, and the description thereof will be omitted.

The device 1 of this embodiment does not include the tubular electrode 33. The second bottom portion 32 of the second electrode member 3 does not have the function of supplying a voltage to the tubular electrode 33 but only has the function of inducing an electric charge to the surface of the first conductor 6. For this reason, an electric charge can be more efficiently induced to the surface of the first conductor 6 by the second bottom portion 32. Note that, as with the fifth embodiment, the first conductor 6 may be provided on the inner surface 102 of the cover 10. In addition, in the device 1 of first embodiment to the sixth embodiment, the tubular electrode 33 may be omitted as with this embodiment.

<Comparative Experiments>

The present inventors have conducted comparative experiments on the straightness of the fiber to be sprayed by using a comparative example, and the electrostatic spinning device as the electrostatic spray device 1 of the embodiments. The comparative example is a device having the same configuration as that of the first embodiment except that the first conductor 6 is not provided. In each of the experiments, the range of the film that was formed by the fiber to be sprayed covering the target was measured. The shape of the film was regarded as an elliptical shape, and an area S (mm$^2$) of the film was obtained by Long Radius× Short Radius×Circular Constant. Hereinafter, the diameter of the inner edge of the first conductor 6 is the inner diameter d1 (mm). The diameter of the inner edge of the second conductor 7 is the inner diameter d2 (mm). An aluminum tape having a thickness of 0.5 mm was used as each of the conductors. A mixed solution of 87.6 mass % of ethanol, 12.0 mass % of polyvinyl butyral (manufactured by SEKISUI CHEMICAL CO., LTD.: Product Name S-LEC BM-1), and 0.4 mass % of ion exchange water was used as the spinning liquid.

[Experiment 1]
  Target: Aluminum Foil
  Distance to Target: 100 mm
  Temperature in Environment: 24° C.
  Relative Humidity in Environment: 40% RH
  Voltage: 14.5 kV
  Flow Rate (Ejection Amount) of Liquid Composition: 0.05 ml/min
  Spray Time: 1 min The area S of the comparative example was 3829. In the device 1 (FIG. 3) of the first embodiment, the inner diameter d1 was changed in a range of 14 to 18, and as a result thereof, the area S was 2376 without being changed in d1=14 to 16, and the area S was 3572 in d1=18. In the device 1 (FIG. 7) of the second embodiment, the inner diameter d2 was changed in a range of 16 to 20, and as a result thereof, the area S was 3318 without being changed. In the device 1

(FIG. 9) of the fourth embodiment, the inner diameter d2 was 16, and the inner diameter d1 was changed in a range of 14 to 18, and as a result thereof, the area S was 2376 without being changed in d1=14 to 16, and the area S was 1964 in d1=18. The inner diameter d2 was 20, and the inner diameter d1 was changed in a range of 14 to 18, and as a result thereof, the area S was 1964 in d1=14 and d1=18, and the area S was 2828 in d1=16.

[Experiment 2]
    Target: Aluminum Foil
    Distance to Target: 120 mm
    Temperature in Environment: 30° C.
    Relative Humidity in Environment: 85% RH
    Voltage: 14.5 kV
    Flow Rate (Ejection Amount) of Liquid Composition: 0.05 ml/min
    Spray Time: 1 min The area S of the comparative example was 2649. In the device (FIG. 7) of the second embodiment, the second conductor 7 having the inner diameter d2 of 20 was used, and as a result thereof, the area S was 2355. In the device (FIG. 9) of the fifth embodiment, the first conductor 6 having the inner diameter d1 of 14 and the second conductor 7 having the inner diameter d2 of 20 were used, and as a result thereof, the area S was 1766.

[Experiment 3]
    Target: Back of Human Hand
    Distance to Target: 120 mm
    Temperature in Environment: 30° C.
    Relative Humidity in Environment: 85% RH
    Voltage: 14.5 kV
    Flow Rate (Ejection Amount) of Liquid Composition: 0.05 ml/min
    Spray Time: 1 min The area S of the comparative example was 3297, and a deposition state on the back of the hand was not homogeneous. In the device (FIG. 9) of the fourth embodiment, the first conductor 6 having the inner diameter d1 of 14 and the second conductor 7 having the inner diameter d2 of 20 were used, and as a result thereof, the area S was 1570, and a deposition state on the back of the hand was homogeneous.

[Discussion]

From Experiments 1 to 3 described above, it is found that in the device 1 of each of the embodiments, in general, the area S is small, in other words, the spray range in the target is small, and the density is high, compared to the comparative example. Accordingly, it is found that the device 1 includes the first conductor 6 or the second conductor 7, and thus, the straightness of the fiber is improved, and thus, the fiber efficiently reaches the target, and the adhesiveness or the homogeneousness of the film to be formed is improved.

From Experiment 1, it is found that there is a case where the area S of the device 1 (FIG. 3) of the first embodiment can be smaller than that of the device 1 (FIG. 7) of the second embodiment. From this, it is suggested that it is advantageous that a distance between the conductor and the second bottom portion 32 is small since an electric charge can be more efficiently induced to the surface of the conductor. Alternatively, it is suggested that it is advantageous that the conductor is disposed in the position overlapping with the tip 530 of the needle-shaped electrode 53 or on the second bottom portion 32 side from the tip 530 since the function of the needle-shaped electrode 53 for forming the electric field is not weakened by the electric charge of the conductor.

From Experiment 1, it is found that there is a case where the area S of the device 1 (FIG. 9) of the fourth embodiment can be smaller than that of the device 1 (FIG. 3) of the first embodiment and the device 1 (FIG. 7) of the second embodiment. From Experiment 2, it is found that there is a case where the area S of the device 1 (FIG. 9) of the fifth embodiment can be smaller than that of the device 1 (FIG. 7) of the second embodiment. From this, it is suggested that it is advantageous to include a plurality of conductors since many electric charges can be more efficiently induced to the surface of the outermost conductor.

As described above, the preferred embodiments of the present invention have been described in detail with reference to the accompanying drawings, but the technical scope of the present invention is not limited to such examples. It is obvious for a person with ordinary skill in the art of the present invention that various modification example or correction examples can be conceived within the category of the technical idea described in the claims, and it is obviously understood that such examples also belong to the technical scope of the present invention.

For example, a gap (the air) but not the insulator such as the housing or the cover may be simply interposed between the conductor and the electrode member or in the plurality of conductors, and thus, the conductor and the electrode member or the plurality of conductors may be electrically isolated and separated from each other.

Regarding the above-described embodiments, the present invention also includes the following electrostatic spray device, cartridge, and cover.

<1>

A hand-held type electrostatic spray device which has a shape or a size that a user is capable of retaining with a hand and sprays an electrically charged liquid, the electrostatic spray device comprising: a voltage source; a base electrode for electrically charging the liquid to which a voltage is applied from the voltage source and which includes a linear tip portion; an additional electrode to which a voltage is applied from the voltage source; and a conductor which is electrically isolated from the base electrode and the additional electrode and is disposed on a spray side of the liquid from the additional electrode, at least a part of the conductor overlapping with the additional electrode in a direction orthogonal to a spray direction of the liquid.

<2>

The electrostatic spray device according to <1> described above, in which the conductor is disposed along a circumference of the tip portion of the base electrode.

<3>

The electrostatic spray device according to <1> or <2> described above, in which at least a part of the conductor includes a surface expanding along the direction orthogonal to the spray direction of the liquid.

<4>

The electrostatic spray device according to any one of <1> to <3> described above, further comprising: a cartridge, in which the cartridge includes a cartridge side housing which is an insulator containing the base electrode and the additional electrode, and the conductor is provided on an outer surface of the cartridge side housing.

<5>

The electrostatic spray device according to <4> described above, in which the cartridge further includes a nozzle, and the conductor is disposed along a circumference of the nozzle on the additional electrode side from a tip portion of the nozzle.

<6>

The electrostatic spray device according to any one of <1> to <5> described above, further comprising: a main body side housing which contains the voltage source; a nozzle which protrudes from an outer surface of the main body side housing; and a cover which is an insulator covering the circumference of the nozzle on the outer surface of the main body side housing, in which the conductor is provided on an outer surface or an inner surface of the cover.

<7>

The electrostatic spray device according to any one of <1> to <6> described above, in which two or more conductors are electrically isolated from each other and are disposed to overlap with each other in the direction orthogonal to the spray direction of the liquid.

<8>

The electrostatic spray device according to any one of <1> to <7> described above, further comprising: a tubular electrode to which a voltage is applied from the voltage source and which surrounds the tip portion of the base electrode, in which the conductor is disposed along a circumference of the tubular electrode.

<9>

The electrostatic spray device according to any one of <1> to <8> described above, in which the liquid is a solution in which a high-molecular compound that is capable of forming a fiber is dissolved in a solvent.

<10>

The electrostatic spray device according to any one of <1> to <9> described above, in which a deposited material of the fiber is formed on a surface of a target by an electrostatic spray method.

<11>

The electrostatic spray device according to any one of <1> to <10> described above, further comprising: a main body side housing; a cover; and a cartridge, in which the main body side housing is formed of an insulating material.

<12>

The electrostatic spray device according to any one of <1> to <11> described above, in which the base electrode is provided within a passage from a container containing the liquid to the nozzle.

<13>

The electrostatic spray device according to any one of <1> to <12> described above, further comprising: a first electrode member which includes a first bottom portion, a first wall portion, a needle-shaped electrode, a container connection portion, and a terminal, in which the needle-shaped electrode functions as the base electrode.

<14>

The electrostatic spray device according to any one of <1> to <13> described above, in which at least a part of the additional electrode (a second bottom portion) includes a surface expanding along the direction orthogonal to the spray direction of the liquid.

<15>

The electrostatic spray device according to any one of <1> to <14> described above, further comprising: a tubular electrode which protrudes toward the nozzle side from the additional electrode (the second bottom portion).

<16>

The electrostatic spray device according to any one of <1> to <15> described above, further comprising: a second electrode member which is formed of a conductive material, in which the second electrode member includes a second wall portion, a second bottom portion, and a tubular electrode, and the second bottom portion functions as the additional electrode.

<17>

The electrostatic spray device according to any one of <1> to <16> described above, in which the conductor is a thin film-shaped member formed of a conductive material.

<18>

The electrostatic spray device according to any one of <1> to <17> described above, in which the conductor is formed in the shape of a ring in a circumference direction of an axis of the nozzle.

<19>

The electrostatic spray device according to any one of <1> to <18> described above, in which the conductor is disposed in a range of greater than or equal to 180 degrees in a circumference direction of the tip portion of the base electrode.

<20>

The electrostatic spray device according to any one of <1> to <19> described above, in which the conductor is disposed in a position overlapping with a tip of the base electrode or in the additional electrode side from the tip, in a direction along the spray direction of the liquid.

<21>

The electrostatic spray device according to any one of <1> to <20> described above, in which the conductor is supported by an insulator.

<22>

The electrostatic spray device according to any one of <1> to <21> described above, in which the conductor includes a first conductor, and a second conductor that is disposed on the tip portion side of the nozzle from the first conductor, and an outer diameter of the second conductor is formed to be larger than an outer diameter of the first conductor.

<23>

The electrostatic spray device according to any one of <1> to <22> described above, in which the conductor includes the first conductor, and the second conductor that is disposed on the tip portion side of the nozzle from the first conductor, and an inner diameter of an inner edge of the first conductor is formed to be smaller than an inner diameter of an inner edge of the second conductor.

<24>

A cartridge of a hand-held type electrostatic spray device which has a shape or a size that a user is capable of retaining with a hand and sprays an electrically charged liquid, the cartridge comprising: a base electrode for electrically charging the liquid to which a voltage is capable of being applied from a voltage source and which includes a linear tip portion; an additional electrode to which a voltage is capable of being applied from the voltage source; and a conductor which is electrically isolated from the base electrode and the additional electrode and is disposed on a spray side of the liquid from the additional electrode, at least a part of the conductor overlapping with the additional electrode in a direction orthogonal to a spray direction of the liquid.

<25>

The cartridge according to <24> described above, further comprising: a mounting portion; a nozzle; and a container which contains the liquid.

<26>

The cartridge according to <24> or <25> described above, further comprising: a cartridge side housing which is an insulator containing the base electrode and the additional electrode, in which the conductor is provided on an outer surface of the cartridge side housing.

<27>

A cover of a hand-held type electrostatic spray device which has a shape or a size that a user is capable of retaining with a hand and sprays an electrically charged liquid, a main body of the electrostatic spray device, including: a voltage source; a base electrode for electrically charging the liquid to which a voltage is applied from the voltage source and which includes a linear tip portion; and an additional electrode to which a voltage is applied from the voltage source, the cover being attachable and detachable with respect to the main body, the cover comprising a conductor, and the conductor being disposed on a spray side of the liquid from the additional electrode and being electrically isolated from the base electrode and the additional electrode, and at least a part of the conductor overlapping with the additional electrode in a direction orthogonal to a spray direction of the liquid, in a state in which the cover is mounted on the main body.

<28>

The cover according to <27> described above, in which the cover is formed of an insulating material.

<29>

The cover according to <27> or <28> described above, further comprising: a hole through which a nozzle of a cartridge mounted on the electrostatic spray device passes.

<30>

The cover according to <29> described above, in which the conductor is provided on a circumference of the hole.

<31>

The cover according to any one of <27> to <30> described above, in which the conductor is provided on an outer surface of the cover.

<32>

The cover according to any one of <27> to <31> described above, in which the conductor is provided on an inner surface of the cover.

REFERENCE SIGNS LIST

1 Electrostatic spray device
10 Cover
101 Outer surface
102 Inner surface
11 Main body side housing
2 Cartridge
2B Nozzle
20 Cartridge side housing
32 Second bottom portion (additional electrode)
33 Tubular electrode
53 Needle-shaped electrode (base electrode)
6 First conductor
7 Second conductor

The invention claimed is:

1. A hand-held type electrostatic spray device which has a shape or a size that a user is capable of retaining with a hand and sprays an electrically charged liquid, the electrostatic spray device comprising:
   a voltage source;
   a base electrode for electrically charging the liquid to which a voltage is applied from the voltage source and which includes a linear tip portion;
   an additional electrode to which a voltage is applied from the voltage source; and
   a conductor which is electrically isolated from the base electrode and the additional electrode and is disposed apart with respect to the additional electrode in a spray direction of the liquid,
   wherein at least a part of the conductor overlaps with the additional electrode viewed from a direction along the spray direction of the liquid, and
   wherein the conductor is disposed along a circumference of the tip portion of the base electrode.

2. The electrostatic spray device according to claim 1, wherein at least a part of the conductor includes a surface expanding along the direction orthogonal to the spray direction of the liquid.

3. The electrostatic spray device according to claim 1, further comprising:
   a cartridge,
   wherein the cartridge includes a cartridge side housing which is an insulator containing the base electrode and the additional electrode, and
   the conductor is provided on an outer surface of the cartridge side housing.

4. The electrostatic spray device according to claim 3, wherein the cartridge further includes a nozzle, and
   the conductor is disposed along a circumference of the nozzle on the additional electrode side from a tip portion of the nozzle.

5. The electrostatic spray device according to claim 1, further comprising:
   a main body side housing which contains the voltage source;
   a nozzle which protrudes from an outer surface of the main body side housing; and
   a cover which is an insulator covering the circumference of the nozzle on the outer surface of the main body side housing,
   wherein the conductor is provided on an outer surface or an inner surface of the cover.

6. The electrostatic spray device according to claim 1, wherein the liquid is a solution in which a high-molecular compound that is capable of forming a fiber is dissolved in a solvent.

7. The electrostatic spray device according to claim 1, wherein a deposited material of a fiber is formed on a surface of a target by an electrostatic spray method.

8. The electrostatic spray device according to claim 1, further comprising:
   a main body side housing;
   a cover; and
   a cartridge,
   wherein the main body side housing is formed of an insulating material.

9. The electrostatic spray device according to claim 1, wherein the base electrode is provided within a passage from a container containing the liquid to a nozzle.

10. The electrostatic spray device according to claim 1, further comprising:
    a first electrode member which includes a first bottom portion, a first wall portion, a needle-shaped electrode, a container connection portion, and a terminal,
    wherein the needle-shaped electrode functions as the base electrode.

11. The electrostatic spray device according to claim 1, wherein at least a part of the additional electrode includes a surface expanding along the direction orthogonal to the spray direction of the liquid.

12. The electrostatic spray device according to claim 1, further comprising:
    a tubular electrode which protrudes toward a nozzle side from the additional electrode,
    wherein the tubular electrode is connected to the additional electrode.

13. The electrostatic spray device according to claim 1, further comprising:

a second electrode member which is formed of a conductive material, wherein the second electrode member includes a second wall portion, a second bottom portion, and a tubular electrode, wherein the second bottom portion functions as the additional electrode, and wherein the tubular electrode and the additional electrode are portions of the second electrode member.

14. The electrostatic spray device according to claim 1, wherein the conductor is formed in the shape of a ring in a circumference direction of an axis of a nozzle.

15. The electrostatic spray device according to claim 1, wherein the conductor is disposed in a position overlapping with a tip of the base electrode or in the additional electrode side from the tip, in a direction along the spray direction of the liquid.

16. A hand-held type electrostatic spray device which has a shape or a size that a user is capable of retaining with a hand and sprays an electrically charged liquid, the electrostatic spray device comprising:

a voltage source;

a base electrode for electrically charging the liquid to which a voltage is applied from the voltage source and which includes a linear tip portion;

an additional electrode to which a voltage is applied from the voltage source; and two or more conductors which are electrically isolated from the base electrode and the additional electrode and are disposed apart with respect to the additional electrode in a spray direction of the liquid, wherein at least a part of the two or more conductors overlaps with the additional electrode viewed from a direction along the spray direction of the liquid, and wherein the two or more conductors are electrically isolated from each other and are disposed to overlap with each other viewed from a direction along the spray direction of the liquid.

17. A hand-held type electrostatic spray device which has a shape or a size that a user is capable of retaining with a hand and sprays an electrically charged liquid, the electrostatic spray device comprising:

a voltage source;

a base electrode for electrically charging the liquid to which a voltage is applied from the voltage source and which includes a linear tip portion;

an additional electrode to which a voltage is applied from the voltage source; and a conductor which is electrically isolated from the base electrode and the additional electrode and is disposed apart with respect to the additional electrode in a spray direction of the liquid, wherein at least a part of the conductor overlaps with the additional electrode viewed from a direction along the spray direction of the liquid, wherein the electrostatic spray device further comprises a tubular electrode to which a voltage is applied from the voltage source and which surrounds the tip portion of the base electrode, wherein the tubular electrode is connected to the additional electrode, and wherein the conductor is disposed along a circumference of the tubular electrode.

* * * * *